US006458537B1

(12) United States Patent
Staub et al.

(10) Patent No.: US 6,458,537 B1
(45) Date of Patent: Oct. 1, 2002

(54) METHODS OF DNA TYPING WITH TANDEM REPEATS

(75) Inventors: Rick W Staub, Sugar Land; Michael G. Carrico, Missouri City, both of TX (US)

(73) Assignee: Identigene, Houston, TX (US)

( * ) Notice: Subject to any disclaimer, the term of this patent is extended or adjusted under 35 U.S.C. 154(b) by 0 days.

(21) Appl. No.: 09/395,604

(22) Filed: Sep. 14, 1999

Related U.S. Application Data

(60) Provisional application No. 08/637,115, filed on Apr. 24, 1996, now Pat. No. 5,994,064.

(51) Int. Cl.[7] .............................. C12Q 1/68; C12P 19/34; C07H 19/00
(52) U.S. Cl. ..................... 435/6; 435/91.1; 435/91.2; 536/22.1
(58) Field of Search .................... 435/6, 91.1, 91.2; 536/22.1, 24.3

(56) References Cited

U.S. PATENT DOCUMENTS 5,364,759 A 11/1994 Caskey .................... 536/24.31

OTHER PUBLICATIONS

Alford R.L., et al., *Am. J. Hum. Genet.*, 55(190):190–5 (1994).
Clayton T.M., et al., *Forens. Sci. Int'l*, 76:17–25 (1995).
Corach D, et al., *Electrophoresis*, 16:1617–23 (1995).
Edwards A., et al., *Am. J. Hum. Genet.*, 49:746–56 (1991).
Evett I.W., et al., *Am. J. Hum. Genet.*, 58:398–407 (1996).
Gill P., et al., *Electrophoresis*, 16:1543–52 (1995).
Hammond H.A., et al., *Am. J. Hum. Genet.*, 55:175–89 (1994).
Holgersson S. et al., *Electrophoresis*, 15(7):890–5 (1994).
Huang N.E., et al., *Foren. Sci. Int'l*, 71:131–6 (1995).
Kimptom C. et al., *Foren. Sci. Int'l*, 71(2):137–52 (1995).
Kimpton C., et al., in *PCR Methods and Applications*, 13–22 (1993).
Moller A. & Brinkmann B., *Int. J. Legal Med.*, 106(5):262–7 (1994).
Puers C., et al., *Am. J. Hum. Gent.*, 53:000–000 (1993).
SharmaV. & Litt M., *Hum. Mol. Genet.*, 1:67 (1992).
Urquhart A., et al., *Int. J. Legal Med.*, 107:13–20 (1994).

*Primary Examiner*—Gary Benzion
*Assistant Examiner*—Joyce Tung
(74) *Attorney, Agent, or Firm*—Baker Botts LLP

(57) ABSTRACT

Methods useful for multiplex amplifying a plurality of loci or genetic systems comprise at least two loci. The at least two loci may be selected from the group consisting of D9S302, D22S683, D18S535, D3S2387, D4S2366, D5S1719 and D7S1804 loci. In another embodiment, preferably at least two loci comprise complex tandem repeat (CTR) sequences. The methods, kits, compositions and ladders disclosed herein are useful for analyzing human samples, as well as samples from other species. Analysis includes parentage, forensic, tissue origin, sample origin and genetic relatedness studies.

29 Claims, 11 Drawing Sheets

FIGURE 1A

| LOCUS | MULTIPLEX A | | | | | MULTIPLEX B | | | | | |
|---|---|---|---|---|---|---|---|---|---|---|---|
| | D9S302 | D22S683 | D18S535 | TOTAL A | | D7S1804 | D3S2387 | D4S2366 | D5S1719 | TOTAL B | |
| CAUCASIAN | | | | | | | | | | | |
| HOMOZYGOSITY | 0.0922 | 0.1000 | 0.2266 | | | 0.1280 | 0.1440 | 0.2170 | 0.1480 | | |
| HETEROZYGOSITY | 0.9078 | 0.9000 | 0.7734 | | | 0.8720 | 0.8560 | 0.7830 | 0.8520 | | |
| POE | 0.8114 | 0.7954 | 0.5506 | 0.9827 | | 0.7387 | 0.7067 | 0.5679 | 0.6988 | 0.9900 | |
| RMNE | 0.1886 | 0.2046 | 0.4494 | 0.0173 | | 0.2613 | 0.2933 | 0.4321 | 0.3012 | 0.0100 | |
| BLACK | | | | | | | | | | | |
| HOMOZYGOSITY | 0.0807 | 0.0710 | 0.2122 | | | 0.0910 | 0.0800 | 0.2420 | 0.1400 | | |
| HETEROZYGOSITY | 0.9193 | 0.9290 | 0.7878 | | | 0.9090 | 0.9200 | 0.7580 | 0.8600 | | |
| POE | 0.8350 | 0.8550 | 0.5766 | 0.9899 | | 0.8138 | 0.8364 | 0.5236 | 0.7147 | 0.9959 | |
| RMNE | 0.1650 | 0.1450 | 0.4234 | 0.0101 | | 0.1862 | 0.1636 | 0.4764 | 0.2853 | 0.0041 | |
| HISPANIC | | | | | | | | | | | |
| HOMOZYGOSITY | 0.0867 | 0.1090 | 0.2383 | | | 0.1190 | 0.1220 | 0.1680 | 0.3280 | | |
| HETEROZYGOSITY | 0.9133 | 0.8910 | 0.7617 | | | 0.8810 | 0.8780 | 0.8320 | 0.6720 | | |
| POE | 0.8227 | 0.7771 | 0.5300 | 0.9814 | | 0.7568 | 0.7507 | 0.6597 | 0.3863 | 0.9873 | |
| RMNE | 0.1773 | 0.2229 | 0.4700 | 0.0186 | | 0.2432 | 0.2493 | 0.3403 | 0.6137 | 0.0127 | |
| ASIAN | | | | | | | | | | | |
| HOMOZYGOSITY | 0.0819 | 0.1650 | 0.2080 | | | 0.1290 | 0.1290 | 0.2130 | 0.2040 | | |
| HETEROZYGOSITY | 0.9181 | 0.8350 | 0.7920 | | | 0.8710 | 0.8710 | 0.7870 | 0.7960 | | |
| POE | 0.8325 | 0.6655 | 0.5843 | 0.9767 | | 0.7366 | 0.7366 | 0.5751 | 0.5916 | 0.9880 | |
| RMNE | 0.1675 | 0.3345 | 0.4157 | 0.0233 | | 0.2634 | 0.2634 | 0.4249 | 0.4084 | 0.0120 | |
| JAPANESE | | | | | | | | | | | |
| HOMOZYGOSITY | 0.0980 | 0.1490 | 0.2108 | | | 0.1220 | 0.1510 | 0.2070 | 0.2840 | | |
| HETEROZYGOSITY | 0.9020 | 0.8510 | 0.7892 | | | 0.8780 | 0.8490 | 0.7930 | 0.7160 | | |
| POE | 0.7995 | 0.6968 | 0.5792 | 0.9744 | | 0.7507 | 0.6929 | 0.5861 | 0.4534 | 0.9827 | |
| RMNE | 0.2005 | 0.3032 | 0.4208 | 0.0256 | | 0.2493 | 0.3071 | 0.4139 | 0.5466 | 0.0173 | |

FIGURE 1B

| LOCUS | MULTIPLEX C | | | | | TOTAL | TOTAL for MULTIPLEX |
|---|---|---|---|---|---|---|---|
| | CSF1PO | FESFPS | TH01 | LIPOL | | C | A, B, C |
| CAUCASIAN | | | | | | | |
| HOMOZYGOSITY | 0.2710 | 0.3080 | 0.2200 | 0.3080 | | | |
| HETEROZYGOSITY | 0.7290 | 0.6920 | 0.7800 | 0.6920 | | | |
| POE | 0.4745 | 0.4160 | 0.5625 | 0.4160 | | 0.9216 | 0.999986 |
| RMNE | 0.5255 | 0.5840 | 0.4375 | 0.5840 | | 0.0784 | 0.000014 |
| BLACK | | | | | | | |
| HOMOZYGOSITY | 0.2180 | 0.2500 | 0.2450 | 0.2580 | | | |
| HETEROZYGOSITY | 0.7820 | 0.7500 | 0.7550 | 0.7420 | | | |
| POE | 0.5661 | 0.5098 | 0.5184 | 0.4962 | | 0.9484 | 0.999998 |
| RMNE | 0.4339 | 0.4902 | 0.4816 | 0.5038 | | 0.0516 | 0.000002 |
| HISPANIC | | | | | | | |
| HOMOZYGOSITY | 0.2850 | 0.3140 | 0.2230 | 0.3390 | | | |
| HETEROZYGOSITY | 0.7150 | 0.6860 | 0.7770 | 0.6610 | | | |
| POE | 0.4518 | 0.4069 | 0.5571 | 0.3705 | | 0.9094 | 0.999979 |
| RMNE | 0.5482 | 0.5931 | 0.4429 | 0.6295 | | 0.0906 | 0.000021 |
| ASIAN | | | | | | | |
| HOMOZYGOSITY | 0.2580 | 0.3120 | 0.2860 | 0.4920 | | | |
| HETEROZYGOSITY | 0.7420 | 0.6880 | 0.7140 | 0.5080 | | | |
| POE | 0.4962 | 0.4099 | 0.4502 | 0.1946 | | 0.8684 | 0.999963 |
| RMNE | 0.5038 | 0.5901 | 0.5498 | 0.8054 | | 0.1316 | 0.000037 |
| JAPANESE | | | | | | | |
| HOMOZYGOSITY | 0.2770 | 0.3290 | 0.2780 | 0.5900 | | | |
| HETEROZYGOSITY | 0.7230 | 0.6710 | 0.7220 | 0.4100 | | | |
| POE | 0.4647 | 0.3848 | 0.4631 | 0.1201 | | 0.8444 | 0.999931 |
| RMNE | 0.5353 | 0.6152 | 0.5369 | 0.8799 | | 0.1556 | 0.000069 |

134 bp Allele:

tcatgtgaca aaagccacac CCATAACTTT TTTCCTCTAG ATAGACAGAT AGAT GATA GATA GATA GATA GATA GATA GATA GATA TAGATTCTCT TTCTC tgcattctca tctatatttc tgtct

FIGURE 2A (SEQ ID NO: 15)

150 bp Allele:

tcatgtgaca aaagccacac CCATAACTTT TTTCCTCTAG ATAGACAGAT AGAT GATA GATA GATA GATA GATA GATA GATA GATA GATA GATA GATA GATA TAGATTCTCT TTCTC tgcattctca tctatatttc tgtct

FIGURE 2B (SEQ ID NO: 16)

176 bp allele:
ggtggaaatg cctcatgtag AAAAAAGGAA AGTTCTGATG TTAGAAAGAG GGGGTCACCT TGAGAGAATG TGGACATGCT GTCTGCTTTA TATA GATA GATA GATA GATA GATA GATA GATA GATA TAGATA TAGATA TAGATA TAGAT tgtttgttt gttttgtttt gtt

FIGURE 3A (SEQ ID NO: 17)

200 bp allele:
ggtggaaatg cctcatgtag AAAAAAGGAA AGTTCTGATG TTAGAAAGAG GGGGTCACCT TGAGAGAATG TGGACATGCT GTCTGCTTTA TATA GATA GATA GATA GATA GATA GATA GATA GATA TAGATA TAGATA TAGATA TAGATA TAGATA TAGAT tgtttgttt gttttgtttt gt

FIGURE 3B (SEQ ID NO: 18)

262 bp allele:
A GATA GATA GAT GATA GATA GAT GATA GATA GATA GATA GATA GATA GATA GAT GATA GATA GATA GAT GATA GATA GATA GATA GAT GATA GA GATA GAT GATA GAT GATA GGTAGGTA GATA GAT GATA GATA GATA GGTA GATA GAT GATA GATA GAT GATA GATA GATA GATA

FIGURE 4A (SEQ ID NO: 19)

274 bp allele:
A GATA GATA GATA GATA GAT GATA GAT GATA GATA GATA GATA GATA GATA GATA TAGAT GATA GATA GATA GATTA GATA GATA GATA GATA GATA GATA GA GATA GAT GATA GAT GATA GGTAGGTA GATA GAT GATA GATA GATA GATA GATA GATA GATA GATA GATA GATA GATA GATA GATGTTAGAT

FIGURE 4B (SEQ ID NO: 20)

191 bp allele (Allele 26):
aaagctagaaggagctggctGTGGGAGTC*TCTCTCTCTCTCTCTCTATCTCCAG*ACAGAGACAG
ACAGATAGATAGATAGATAGATAGATAGATAGATAGATAGATAGATAGATAGATAGACAGA
CAGACAGACAGACAGACAGACAGACAGATAGATAGATATAGAGAGAGATATAGAGAGTCTcacatctcactctgtcaccc

FIGURE 5A (SEQ ID NO: 21)

183 bp allele (Allele 24)
aaagctagaaggagctggctGTGGGAGTC*TCTCTCTCTCTCTCTCTATCTCCAG*ACAGAGACAG
ACAGATAGATAGATAGATAGATAGATAGATAGATAGATAGATAGATAGACAGACAGACAGA
CAGACAGACAGACAGACAGATAGATAGATATAGAGAGAGTCTcacatctcactctgt
caccc

FIGURE 5B (SEQ ID NO: 22)

185 bp allele (Allele 24.2)
aaagctagaaggagctggctGTGGGAGTC*TCTCTCTCTCTCTCTCTCTATCTCCAG*TATCTCCAG
ACAGACAGACAGATAGATAGATAGATAGATAGATAGATAGATAGATAGACAGACAGACAGA
CAGACAGACAGACAGACAGACAGATAGATAGATATAGAGAGAGTCTcacatctcactctgt
caccc

FIGURE 5C (SEQ ID NO: 23)

195 bp allele (Allele 27)
aaagctagaaggagctggctGTGGGAGT*CTCTCTCTCTCTCTCT*ATCTCCAGACACAGACACAGATAGATAGATAGATAGATAGATAGATAGACAGACAGACAGACAGACAGACAGACAGATAGATATAGAGAG AGTCTcacatctcactctgtcaccc

FIGURE 5D (SEQ ID NO: 24)

215 bp allele (Allele 32)
aaagctagaaggagctgtGTGGGAGT*CTCTCTCTCTCTCTCT*ATCTCCAGACACAGACACAGATAGATAGATAGATAGATAGATAGATAGACAGACAGACAGACAGACAGACAGACAGATAGATAGATAGATAGATAGATATAGAGAGTCTcacatctcactctgtcaccc

FIGURE 5E (SEQ ID NO: 25)

131 bp allele (Allele 14)
tcctgacattcctagggtgaACTTCACACATGGTAATTAGAGATGACTGATAGATAAATGGATAGATAGATAGATAGATAGATAGATTGATAGATAGAcgatagagagccatatttgtttt

FIGURE 6A (SEQ ID NO: 26)

123 bp allele (Allele 12)
tcctgacattcctagggtgaACTTCACACATGGTAATTAGAGATGACTGATAGATAAATGGATAGATAGATAGATAGATAGATTGATAGATAGAcgatagagagccatatttgtttt

FIGURE 6B (SEQ ID NO: 27)

143 bp allele (Allele 17)
tcctgacattcctagggtgaACTTCACACATGGTAATTAGAGATGACTGATAGATAAATGGATAGATAGATAGATAGATAGATAGATAGATAGATAGATTGATAGA
cgatagagagccatatttgtttt

FIGURE 6C (SEQ ID NO: 28)

88 bp allele (Allele 7)
gttcatttagagtaacagggccAATTTTAGATAGATAGATAGATAGATAGATAGAGAAGT
AGGCtaagtcccacaatctgccat

FIGURE 7A (SEQ ID NO: 29)

107 bp allele (Allele 11.3)
gttcatttagagtaacagggccAATTTTAGATAGATAGATGATAGATAGATAGATAGATA
GATAGATAGATAGAGAAGTAGGCtaagtcccacaatctgccat

FIGURE 7B (SEQ ID NO: 30)

84 bp allele (Allele 6)
gttcatttagagtaacagggccAATTTTAGATAGATAGATAGATAGATAGAGAAGTAGGC
taagtcccacaatctgccat

FIGURE 7C (SEQ ID NO: 31)

88 bp allele (Allele 7)
gttcatttagagtaacagggccAATTTTAGATAGATAGATAGATAGATAGATAGAGAAGT
AGGCtaagtcccacaatctgccat

FIGURE 7D (SEQ ID NO: 32)

261 bp allele (Allele 28)
tcaagtgttggttcactGTGGAACTTGAGATGGTGACTAGAGTCTAGAGTGGGACCGAGTCTGTAGGATCTAACAGGATCTAAGCCTAGCAAAGCTCTCTATCTATCTATCTGTCTGTCTGTCTGTCTATCTATCTATCTATCTATCTATCAATTATCTATCTATCTATCTATCTATCTATCTATCTATCTACCTATCTATCTATGTCTGAATGGAAacaccactgactagaccca

FIGURE 8A (SEQ ID NO: 33)

237 bp allele (Allele 22)
tcaagtgtttggttcactGTGGAACTTGAGATGGTGACTAGAGTCTAGAGTGGGACCGAGTCTGTAGGATCTAACAGGATCTAAGCCTAGCAAAGCTCTCTATCTATCTGTCTGTCTGTCTGTCTATCTATCTATCTATCTATCAATTATCTATCTATCTACCTATCTATCTATGTCTGAATGGAAacaccactgactagacca

FIGURE 8B (SEQ ID NO: 34)

297 bp allele (Allele 37)
tcaagtgtttggttcactGTGGAACTTGAGATGGTGACTAGAGTCTAGAGTGGGACCGAGTCTGTAGGATCTAACAGGATCTAAGCCTAGCAAAGCTCTCTATCTGTCTGTCTGTCTGTCTGTCTGTCTATCTATTATCTATCTATCAATTATCTATCTATCTATCTATCTATCTATCTATCTATCTATCTATCTATCTATCTATCTATCTATCTATCTATCTATCTATCTATCTATCTATCTATCTATCTATCTACCTATCTATCTATGTCTGAATGGAAacaccactgactagaccca

FIGURE 8C (SEQ ID NO: 35)

289 bp allele (Allele 35)
ttcaagtgttgggttcactGTGGAACTTGAGATGGTGACTAGAGTCTAGAGTGGGACCGAGTCT
GTAGGATCTAACAGGATCTAAGCCTAGCAAAGCTCTATCTGTCTGTCTGTCTGT
CTGTCTGTCTGTCTATCTATCTATCTATCTATCTATCTATCTATCTATCTATCTA
TCTATTATTATCTATCAATTATCTATCTATCTATCTATCTATCTATCTATCTATC
TATCTATCTACCTATCTATCTATGTCTGAATGGAAacaccactgactagaccc

FIGURE 8D (SEQ ID NO: 36)

265 bp allele (Allele 29)
ttcaagtgttgggttcactGTGGAACTTGAGATGGTGACTAGAGTCTAGAGTGGGACCGAGTCT
GTAGGATCTAACAGGATCTAAGCCTAGCAAAGCTCTCTATCTATCTGTCTGTCTGT
CTGTCTATCTATCTATCTATCTATCTATCTATTATCTATCAATTATCTATCTATCT
ATCTATCTATCTATCTATCTATCTATCTATCTACCTATCTATCTATGT
CTGAATGGAAacaccactgactagaccca

FIGURE 8E (SEQ ID NO: 37)

SEQUENCE LISTING

<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: Primer for D18S535

<400> SEQUENCE: 1
tcatgtgaca aaagccacac                                                    20

<210> SEQ ID NO 2
<211> LENGTH: 25
<212> TYPE: DNA
<213> ORGANISM: Artificial Sequence
<220> FEATURE:
<223> OTHER INFORMATION: Primer for D18S535

<400> SEQUENCE: 2
agacagaaat atagatgaga atgca                                              25

<210> SEQ ID NO 3
<211> LENGTH: 23
<212> TYPE: DNA
<213> ORGANISM: Artificial Sequence
<220> FEATURE:
<223> OTHER INFORMATION: Primer for D22S683

<400> SEQUENCE: 3
aacaaaacaa aacaaaacaa aca                                                23

<210> SEQ ID NO 4
<211> LENGTH: 20
<212> TYPE: DNA
<213> ORGANISM: Artificial Sequence
<220> FEATURE:
<223> OTHER INFORMATION: Primer for D22S683

<400> SEQUENCE: 4
ggtggaaatg cctcatgtag                                                    20

<210> SEQ ID NO 5
<211> LENGTH: 20
<212> TYPE: DNA
<213> ORGANISM: Artificial Sequence
<220> FEATURE:
<223> OTHER INFORMATION: Primer for D9S302

<400> SEQUENCE: 5
ggggacagac tccagatacc                                                    20

<210> SEQ ID NO 6
<211> LENGTH: 20
<212> TYPE: DNA
<213> ORGANISM: Artificial Sequence
<220> FEATURE:
<223> OTHER INFORMATION: Primers for D9S302

<400> SEQUENCE: 6
gcgacagagt gaaaccttgt                                                    20

<210> SEQ ID NO 7
<211> LENGTH: 20

```
<212> TYPE: DNA
<213> ORGANISM: Artificial Sequence
<220> FEATURE:
<223> OTHER INFORMATION: Primer for D3S2387

<400> SEQUENCE: 7
aaagctagaa ggagctggct                                           20

<210> SEQ ID NO 8
<211> LENGTH: 20
<212> TYPE: DNA
<213> ORGANISM: Artificial Sequence
<220> FEATURE:
<223> OTHER INFORMATION: Primer for D3S2387

<400> SEQUENCE: 8
gggtgacaga gtgagatgtg                                           20

<210> SEQ ID NO 9
<211> LENGTH: 20
<212> TYPE: DNA
<213> ORGANISM: Artificial Sequence
<220> FEATURE:
<223> OTHER INFORMATION: Primer for D4S2366

<400> SEQUENCE: 9
tcctgacatt cctagggtga                                           20

<210> SEQ ID NO 10
<211> LENGTH: 25
<212> TYPE: DNA
<213> ORGANISM: Artificial Sequence
<220> FEATURE:
<223> OTHER INFORMATION: Primer for D4S2366

<400> SEQUENCE: 10
aaaacaaata tggctctatc tatcg                                     25

<210> SEQ ID NO 11
<211> LENGTH: 22
<212> TYPE: DNA
<213> ORGANISM: Artificial Sequence
<220> FEATURE:
<223> OTHER INFORMATION: Primer for D5S1719

<400> SEQUENCE: 11
gttcatttag agtaacaggg cc                                        22

<210> SEQ ID NO 12
<211> LENGTH: 20
<212> TYPE: DNA
<213> ORGANISM: Artificial Sequence
<220> FEATURE:
<223> OTHER INFORMATION: Primer for D5S1719

<400> SEQUENCE: 12
atggcagatt gtgggactta                                           20

<210> SEQ ID NO 13
<211> LENGTH: 20
<212> TYPE: DNA
<213> ORGANISM: Artificial Sequence
<220> FEATURE:
<223> OTHER INFORMATION: Primer for D7S1804

<400> SEQUENCE: 13
```

```
ttcaagtggt tgggttcact                                                    20

<210> SEQ ID NO 14
<211> LENGTH: 20
<212> TYPE: DNA
<213> ORGANISM: Artificial Sequence
<220> FEATURE:
<223> OTHER INFORMATION: Primer for D7S1804

<400> SEQUENCE: 14
tgggtctagt ccagtggtgt                                                    20

<210> SEQ ID NO 15
<211> LENGTH: 134
<212> TYPE: DNA
<213> ORGANISM: Homo sapiens

<400> SEQUENCE: 15
tcatgtgaca aaagccacac ccataacttt tttcctctag atagacagat agatgataga        60
tagatagata gatagataga tagatagata gatatagatt ctctttctct gcattctcat       120
ctatatttct gtct                                                         134

<210> SEQ ID NO 16
<211> LENGTH: 150
<212> TYPE: DNA
<213> ORGANISM: Homo sapiens

<400> SEQUENCE: 16
tcatgtgaca aaagccacac ccataacttt tttcctctag atagacagat agatgataga        60
tagatagata gatagataga tagatagata gatagataga tagatagata tagattctct       120
ttctctgcat tctcatctat atttctgtct                                        150

<210> SEQ ID NO 17
<211> LENGTH: 176
<212> TYPE: DNA
<213> ORGANISM: Homo sapiens

<400> SEQUENCE: 17
ggtggaaatg cctcatgtag aaaaaaggaa agttctgatg ttagaaagag ggggtcacct        60
tgagagaatg tggacatgct gtctgcttta tatagataga tagatagata gatagataga       120
tagatagata tagatataga tatagatata gattgtttgt tttgttttgt tttgtt          176

<210> SEQ ID NO 18
<211> LENGTH: 200
<212> TYPE: DNA
<213> ORGANISM: Homo sapiens

<400> SEQUENCE: 18
ggtggaaatg cctcatgtag aaaaaaggaa agttctgatg ttagaaagag ggggtcacct        60
tgagagaatg tggacatgct gtctgcttta tatagataga tagatagata gatagataga       120
tagatagata gatagataga tatagatata gatagataga tagatataga tatagattgt       180
ttgttttgtt ttgttttgtt                                                   200

<210> SEQ ID NO 19
<211> LENGTH: 204
<212> TYPE: DNA
<213> ORGANISM: Homo sapiens

<400> SEQUENCE: 19
```

```
agatagatag atagatgata gatagataga tagatagata gatagataga tagatagatg    60
atagatagat gatagataga ttagatagat agatagatag atagatagat agagatagat   120
gatagatgat aggtaggtag atagatgata gatagataga tagatagata ggtagataga   180
tgatagatag atagatgata gata                                          204

<210> SEQ ID NO 20
<211> LENGTH: 213
<212> TYPE: DNA
<213> ORGANISM: Homo sapiens

<400> SEQUENCE: 20
agatagatag atagatagat gatagataga tagatagata gatagataga tatagatgat    60
agatagatga tagatagatt agatagatag atagatagat agatagatag atagagatag   120
atgatagatg ataggtaggt agatagatga tagatagata gatagataga tagatagata   180
gatagataga tgatagatag atagatgtta gat                                213

<210> SEQ ID NO 21
<211> LENGTH: 191
<212> TYPE: DNA
<213> ORGANISM: Homo sapiens

<400> SEQUENCE: 21
aaagctagaa ggagctggct gtgggagtct ctctctctct ctctctctat ctccagacag    60
acagacagat agatagatag atagatagat agatagatag atagatagac agacagacag   120
acagacagac agacagacag acagacagat agatagatat agagagagtc tcacatctca   180
ctctgtcacc c                                                        191

<210> SEQ ID NO 22
<211> LENGTH: 183
<212> TYPE: DNA
<213> ORGANISM: Homo sapiens

<400> SEQUENCE: 22
aaagctagaa ggagctggct gtgggagtct ctctctctct ctctctctat ctccagacag    60
acagacagat agatagatag atagatagat agatagatag atagatagac agacagacag   120
acagacagac agacagacag atagatagat atagagagag tctcacatct cactctgtca   180
ccc                                                                 183

<210> SEQ ID NO 23
<211> LENGTH: 185
<212> TYPE: DNA
<213> ORGANISM: Homo sapiens

<400> SEQUENCE: 23
aaagctagaa ggagctggct gtgggagtct ctctctctct ctctctctct ctctctctat    60
ctccagacag acagatagat agatagatag atagatagat agatagatag acagacagac   120
agacagacag acagacagac agatagatag atatagagag agtctcacat ctcactctgt   180
caccc                                                               185

<210> SEQ ID NO 24
<211> LENGTH: 195
<212> TYPE: DNA
<213> ORGANISM: Homo sapiens
```

<400> SEQUENCE: 24

| | | | | | |
|---|---|---|---|---|---|
| aaagctagaa | ggagctggct | gtgggagtct | ctctctctct | ctctctctat | ctccagacag | 60 |
| acagacagat | agatagatag | atagatagat | agatagatag | atagatagac | agacagacag | 120 |
| acagacagac | agacagacag | acagacagac | agatagatag | atatagagag | agtctcacat | 180 |
| ctcactctgt | caccc | | | | | 195 |

<210> SEQ ID NO 25
<211> LENGTH: 215
<212> TYPE: DNA
<213> ORGANISM: Homo sapiens

<400> SEQUENCE: 25

| | | | | | |
|---|---|---|---|---|---|
| aaagctagaa | ggagctggct | gtgggagtct | ctctctctct | ctctctctat | ctccagacag | 60 |
| acagacagat | agatagatag | atagatagat | agatagatag | atagatagat | agatagatag | 120 |
| atagatagat | agacagacag | acagacagac | agacagacag | acagacagac | agatagatag | 180 |
| atatagagag | agtctcacat | ctcactctgt | caccc | | | 215 |

<210> SEQ ID NO 26
<211> LENGTH: 131
<212> TYPE: DNA
<213> ORGANISM: Homo sapiens

<400> SEQUENCE: 26

| | | | | | |
|---|---|---|---|---|---|
| tcctgacatt | cctagggtga | acttcacatg | gtaattagat | gactgataga | taaatggata | 60 |
| gatagataga | tagatagata | gatagataga | tagattgata | gatagacgat | agatagagcc | 120 |
| atatttgttt | t | | | | | 131 |

<210> SEQ ID NO 27
<211> LENGTH: 123
<212> TYPE: DNA
<213> ORGANISM: Homo sapiens

<400> SEQUENCE: 27

| | | | | | |
|---|---|---|---|---|---|
| tcctgacatt | cctagggtga | acttcacatg | gtaattagat | gactgataga | taaatggata | 60 |
| gatagataga | tagatagata | gatagattga | tagatagacg | atagatagag | ccatatttgt | 120 |
| ttt | | | | | | 123 |

<210> SEQ ID NO 28
<211> LENGTH: 143
<212> TYPE: DNA
<213> ORGANISM: Homo sapiens

<400> SEQUENCE: 28

| | | | | | |
|---|---|---|---|---|---|
| tcctgacatt | cctagggtga | acttcacatg | gtaattagat | gactgataga | taaatggata | 60 |
| gatagataga | tagatagata | gatagataga | tagatagata | gatagattga | ttgatagacg | 120 |
| atagatagag | ccatatttgt | ttt | | | | 143 |

<210> SEQ ID NO 29
<211> LENGTH: 88
<212> TYPE: DNA
<213> ORGANISM: Homo sapiens

<400> SEQUENCE: 29

| | | | | | |
|---|---|---|---|---|---|
| gttcatttag | agtaacaggg | ccaattttag | atagatagat | agatagatag | atagatagag | 60 |
| aagtaggcta | agtcccacaa | tctgccat | | | | 88 |

<210> SEQ ID NO 30
<211> LENGTH: 107
<212> TYPE: DNA
<213> ORGANISM: Homo sapiens

<400> SEQUENCE: 30

```
gttcatttag agtaacaggg ccaattttag atagatgata gatagataga tagatagata      60
gatagataga tagatagaga agtaggctaa gtcccacaat ctgccat                   107
```

<210> SEQ ID NO 31
<211> LENGTH: 84
<212> TYPE: DNA
<213> ORGANISM: Homo sapiens

<400> SEQUENCE: 31

```
gttcatttag agtaacaggg ccaattttag atagatagat agatagatag atagagaagt      60
aggctaagtc ccacaatctg ccat                                             84
```

<210> SEQ ID NO 32
<211> LENGTH: 88
<212> TYPE: DNA
<213> ORGANISM: Homo sapiens

<400> SEQUENCE: 32

```
gttcatttag agtaacaggg ccaattttag atagatagat agatagatag atagatagag      60
aagtaggcta agtcccacaa tctgccat                                         88
```

<210> SEQ ID NO 33
<211> LENGTH: 259
<212> TYPE: DNA
<213> ORGANISM: Homo sapiens

<400> SEQUENCE: 33

```
ttcaagtggt tgggttcact gtggaacttg agatggtgac tagagtctag agtgggaccg      60
agtctgtagg atctaacagg atctaagcct agcaaagctc tctatctatc tgtctgtctg     120
tctgtctatc tatctatcta tctatctatc tattatctat caattatcta tctatctatc     180
tatctatcta tctatctatc tatctatcta tctacctatc tatctatgtc tgaatggaaa     240
caccactgga ctagaccca                                                  259
```

<210> SEQ ID NO 34
<211> LENGTH: 235
<212> TYPE: DNA
<213> ORGANISM: Homo sapiens

<400> SEQUENCE: 34

```
ttcaagtggt tgggttcact gtggaacttg agatggtgac tagagtctag agtgggaccg      60
agtctgtagg atctaacagg atctaagcct agcaaagctc tctatctatc tgtctgtctg     120
tctgtctatc tatctatcta tctatctatc tattatctat caattatcta tctatctatc     180
tatctatcta cctatctatc tatgtctgaa tggaaacacc actggactag accca           235
```

<210> SEQ ID NO 35
<211> LENGTH: 294
<212> TYPE: DNA
<213> ORGANISM: Homo sapiens

<400> SEQUENCE: 35

```
tcaagtggtt gggttcactg tggaacttga gatggtgact agagtctaga gtgggaccga      60
gtctgtagga tctaacagga tctaagccta gcaaagctct ctatctgtct gtctgtctgt    120
ctgtctgtct gtctatctat ctatctatct atctatctat ctatctatct atctatctat    180
ctattatcta tcaattatct atctatctat ctatctatct atctatctat ctatctatct    240
atctatctac ctatctatct atgtctgaat ggaaacacca ctggactaga ccca           294

<210> SEQ ID NO 36
<211> LENGTH: 286
<212> TYPE: DNA
<213> ORGANISM: Homo sapiens

<400> SEQUENCE: 36
ttcaagtggt tgggttcact gtggaacttg agatggtgac tagagtctag agtgggaccg      60
agtctgtagg atctaacagg atctaagcct agcaaagctc tctatctgtc tgtctgtctg    120
tctgtctgtc tgtctatcta tctatctatc tatctatcta tctatctatc tatctatcta    180
ttatctatca attatctatc tatctatcta tctatctatc tatctatcta tctatctatc    240
tacctatcta tctatgtctg aatggaaaca ccactggact agaccc                    286

<210> SEQ ID NO 37
<211> LENGTH: 263
<212> TYPE: DNA
<213> ORGANISM: Homo sapiens

<400> SEQUENCE: 37
ttcaagtggt tgggttcact gtggaacttg agatggtgac tagagtctag agtgggaccg      60
agtctgtagg atctaacagg atctaagcct agcaaagctc tctatctatc tgtctgtctg    120
tctgtctatc tatctatcta tctatctatc tattatctat caattatcta tctatctatc    180
tatctatcta tctatctatc tatctatcta tctatctacc tatctatcta tgtctgaatg    240
gaaacaccac tggactagac cca                                             263
```

METHODS OF DNA TYPING WITH TANDEM REPEATS

REFERENCE TO RELATED APPLICATIONS

This application claims priority from and is a continuation of U.S. patent application Ser. No. 08/637,115, filed Apr. 24, 1996, now U.S. Pat. No. 5,994,064.

BACKGROUND

1. Field of the Invention

The present invention relates to a class of minisatellite DNA called "complex tandem repeats" (CTRs), which are of particular benefit in DNA typing applications. The present invention is also directed to a process of DNA typing using multiplex amplification comprising highly polymorphic complex and simple tandem repeat loci. The present invention is useful in analyses including, but not limited to, parentage, forensic, tissue origin, sample origin and genetic relatedness studies.

2. Description of the Background

Short tandem repeat (STR) polymorphisms are commonly used in DNA identification procedures, either as adjuncts to other genetic tests, or as stand-alone tests. Typically, when STRs are used for purposes relating to human identification, they are amplified by a process referred to as multiplex DNA amplification, which comprises amplification of two or more loci in a single reaction. Generally, the resulting amplified fragments are separated by size by polyacrylamide gel electrophoresis (PAGE) for subsequent analysis. The polymorphisms are then typed by determining their size in comparison to either similarly labeled known external standards or differently labeled internal standards. A DNA typing method of this nature, employing simple tandem repeats and PCR amplification, is disclosed in U.S. Pat. No. 5,364,759 (Caskey).

A critical parameter to evaluate when performing DNA typing for paternity analysis is the power of exclusion of the DNA typing method or test. Power of exclusion is the ability of a test to exclude false positive results that may lead to, for example, incorrectly accusing a man in a paternity test. The average or expected power of exclusion can be estimated using gene frequency distributions of systems in Hardy-Weinberg equilibrium (Brenner, C. & Morris, J. W., Paternity Index Calculations in Single Locus Hyper-Variable DNA Probes: Validation and Other Studies, Proceedings for The International Symposium on Human Identification, pp.21–76 (1989)), or by computing methods (Chakravarti, R. et al., Exclusion of Paternity: State of the Art. Am. J. Hu. Genet., 26:477–488 (1974); Garber, R. A. & Morris, J. W., General Equations for the Average Power of Exclusion for Genetic Systems of n Codominant Alleles in One-Parent and No-Parent Cases of Disputed Parentage, in Inclusion Probabilities in Parentage Testing, pp. 277–280 (1983); Chakravarti, A. and Li, C. C., The Effect of Linkage on Paternity Calculations, in Inclusion Probabilities in Parentage Testing, pp. 411–422 (1983)).

The exclusion probabilities of commonly used STR multiplexes are generally in the range of 85–91% for paternity analysis. Typically, at least three STR triplex analyses must be combined to provide a sufficient power of exclusion for most paternity analyses. For example, Alford et al. describe a battery of nine STR loci amplified in three triplexes which yields an exclusion power of 99.75% in Caucasians (Alford, R. L. et al., Rapid and Efficient Resolution of Parentage by Amplification of Short Tandem Repeats, Am. J. Hum. Genet., 55:190–195 (1994)). For comparison, the use of restriction fragment length polymorphic (RFLP) loci generally requires the testing of just one locus to produce the power of exclusion values equivalent to those obtained by analysis of three STR. RFLP analyses do, however, require larger amounts of DNA and time.

The low exclusion probabilities of commonly used STR loci are the most negative aspect of using STRs for paternity testing. The low exclusion probabilities of STR systems do not pose a serious problem in forensic testing in which the frequencies of both alleles of an individual are included in calculating match probabilities. However, in parentage testing only the frequency of the allele shared by the child and alleged parent is used for the probability calculation. Thus, although DNA typing with STR loci is simpler and faster to perform than RFLP and requires smaller quantities of DNA, many laboratories are reluctant to make the switch because of the sacrifice in exclusion power and accuracy.

Another disadvantage of the current STR multiplex DNA typing systems is that the amplification is rarely, if ever, clean. In other words, there is a considerable production of spurious bands thought to be a result of DNA polymerase slippage and mis-priming (see e.g., Tautz D., Hypervariability of Simple Sequences as a General Source for Polymorphic DNA Markers, Nuc. Acids Res., 17(16) 6463–70 (1989)).

These and other disadvantages are overcome by the methods of the present invention directed to DNA typing by multiplex amplification of highly polymorphic microsatellite loci.

SUMMARY OF THE INVENTION

In accordance with the present invention, powerful methods useful for DNA typing are provided. One embodiment of the present invention is directed to a method of multiplex amplifying comprising a plurality of loci, wherein at least one locus of the plurality is selected from the D3S2387, D4S2366, D5S1719 and D7S1804 loci of DNA. The plurality may further comprise the D18S535, D22S683 and D9S302 loci.

Another embodiment of the present invention is directed to a method of DNA typing comprising multiplex amplifying comprising two or more complex tandem repeat-containing loci referred to as "complex tandem repeats" or CTRs. The CTR loci of the present invention may be selected from the group consisting of D9S302, D22S683, D3S2387, D4S2366, D5S1719 and D7S1804.

Another embodiment of the invention is directed to an allelic ladder useful in DNA typing. The ladders of the present invention may comprise at least 4 alleles from at least one locus selected from the group of loci consisting of D9S302, D18S535, D22S683, D3S2387, D4S2366, D5S1719 and D7S1804.

Another embodiment of the invention is directed to a composition comprising a plurality of amplified loci wherein at least two of said plurality are selected from the group consisting of D9S302, D22S683, D18S535. The plurality may further comprise the D3S2387, D4S2366, D5S1719 and D7S1804 loci. In a preferred embodiment, the plurality of loci of the composition comprises each of the D9S302, D22S683, D18S535, D3S2387, D4S2366, D5S1719 and D7S1804 loci.

Another embodiment of the present invention is directed to a kit for multiplex amplifying DNA comprising a plurality of loci wherein at least one locus of the plurality is selected from the group consisting of D3S2387, D4S2366, D5S1719 and D7S1804.

DESCRIPTION OF THE DRAWINGS

FIG. 1 Statistical data obtained by multiplex amplifying loci of the present invention.

FIG. 2(A) Sequence of the 134 bp D18S535 allele (SEQ ID NO: 15).

FIG. 2(B) Sequence of the 150 bp D18S535 allele (SEQ ID NO: 16).

FIG. 3(A) Sequence of the 176 bp D22S683 allele (SEQ ID NO: 17).

FIG. 3(B) Sequence of the 200 bp D22S683 allele (SEQ ID NO: 18).

FIG. 4(A) Sequence of the 262 bp D9S302 allele (SEQ ID NO: 19).

FIG. 4(B) Sequence of the 274 bp D9S302 allele (SEQ ID NO: 20).

FIG. 5(A) Sequence of the 191 bp D3S2387 allele (SEQ ID NO: 21).

FIG. 5(B) Sequence of the 183 bp D3S2387 allele (SEQ ID NO: 22).

FIG. 5(C) Sequence of the 184 bp D3S2387 allele (SEQ ID NO: 23).

FIG. 5(D) Sequence of the 195 bp D3S2387 allele (SEQ ID NO: 24).

FIG. 5(E) Sequence of the 215 bp D3S2387 allele (SEQ ID NO: 25).

FIG. 6(A) Sequence of the 131 bp D4S2366 allele (SEQ ID NO: 26).

FIG. 6(B) Sequence of the 123 bp D4S2366 allele (SEQ ID NO: 27).

FIG. 6(C) Sequence of the 143 bp D4S2366 allele (SEQ ID NO: 28).

FIG. 7(A) Sequence of the 88 bp D5S1719 allele (SEQ ID NO: 29).

FIG. 7(B) Sequence of the 107 bp D5S1719 allele (SEQ ID NO: 30).

FIG. 7(C) Sequence of the 84 bp D5S1719 allele (SEQ ID NO: 31).

FIG. 7(D) Sequence of the 88 bp D5S1719 allele (SEQ ID NO: 32).

FIG. 8(A) Sequence of the 259 bp D7S1804 allele (SEQ ID NO: 33).

FIG. 8(B) Sequence of the 237 bp D7S1804 allele (SEQ ID NO: 34).

FIG. 8(C) Sequence of the 297 bp D7S1804 allele (SEQ ID NO: 36).

FIG. 8(D) Sequence of the 289 bp D7S1804 allele (SEQ ID NO: 36).

FIG. 8(E) Sequence of the 265 bp D7S1804 allele (SEQ ID NO: 37).

DETAILED DESCRIPTION OF THE INVENTION

The present invention is directed to DNA multiplex amplifying. Multiplex amplifying, as defined herein, refers to a process of amplifying at least two loci in a single amplification reaction. Loci may also be referred to as genetic systems. Thus, multiplex amplifying comprises amplification of at least two genetic systems in a single reaction.

One embodiment of the present invention is directed to a method of multiplex amplifying comprising a plurality of loci, wherein at least one locus of the plurality of loci is selected from the group consisting of D3S2387, D4S2366, D5S1719 and D7S1804. In a preferred embodiment, the plurality comprises at least three of the D3S2387, D4S2366, D5S1719 and D7S1804 genetic systems. The plurality may further comprise at least one locus selected from the group consisting of D9S302, D22S683, D18S535. Preferably, the plurality comprises each of the D9S302, D22S683, D18S535 genetic systems. The plurality may also comprise at least one locus selected from the CSFIPO, FESFPS, TH01 and LIPOL genetic systems. In a particularly preferred embodiment, the plurality of loci of the present invention comprises each of the D3S2387, D4S2366, D5S1719, D7S1804, D9S302, D22S683, D18S535, CSFIPO, FESFPS, TH01 and LIPOL genetic systems co-amplified in a single reaction.

Another embodiment of the invention is directed to the use of a new class of extremely polymorphic loci, termed herein "complex tandem repeats" (CTR), for DNA typing analyses. This embodiment of the invention is directed to a method of multiplex amplifying two or more complex tandem repeat loci, wherein the complex tandem repeats each have heterozygosities ranging from about 83% to about 93%. The complex tandem repeat loci also may contain a GATA motif.

The complex tandem repeats of the present invention include the D9S302, D22S683, D3S2387, D4S2366, D5S1719 and D7S1804 loci. The repeat sequences of these loci are more complex than a simple head to tail repeat of a 2–7 nucleotide sequence. In a preferred embodiment, multiplex amplifying comprises at least two or more loci, wherein at least one locus is selected from the group consisting of the D9S302, D22S683, D3S2387, D4S2366, D5S1719 and D7S1804 loci.

Three classes of CTRs are provided herein. Class I CTRs comprise dual tandem repeats, wherein any number of one type of repeat is followed by any number of a second type of repeat. Class II CTRs comprise islands of a simple repeat sequence separated by short sections of non-repeat sequence sections. Class III CTRs are those that show more complexity than a simple tandem repeat locus, but are not specifically Class I or Class II CTRs.

D3S2387 (D3) is a Class III CTR and consists of a stretch of CT dinucleotide repeats followed by a non-repeat island of ATCTCCA followed by a stretch of GACA and GATA repeats. Variability is present in the number of GACA/GATA repeats, as well as the number of CT dinucelotide repeats. The additional level of complexity of this locus probably accounts for its high degree of heterozygosity (84.9%–92.0%).

D4S2366 (D4) is a Class III CTR and consists of GATA repeats interrupted by a non-repeat island of an AATG sequence. There is variability in the number of GATA repeats from D4 allele to D4 allele. Some D4 alleles also contain a single nucleotide polymorphism, wherein a GATT sequence is amidst the GATA repeats. The level of complexity produces a range of heterozygosity from about 75.8% to 83.2%.

D5S1719 (D5) is a Class III CTR and comprises a sequence of GATA repeats which can be interrupted by a GAT repeat. The complexity of this locus produces heterozygosities ranging from about 67.2% to about 86.0%.

D7S1804 (D7) is a Class III CTR with a string of GATA and GACA repeats of interrupted by islands of non-repeat DNA sequences. Variability exists in the number of GATA/GACA repeats between different D7 alleles. The level of complexity produces a range of heterozygosity from about 87.1% to 90.9%.

D9S302 (D9) is a Class II CTR and is even more complex, containing GATA repeats interspersed with a variety of sequences, including GAT, GATT, TAGAT, and more complicated variations. This high level of complexity is reflected by a very high heterozygosity (90.2%–91.9%) and contributes greatly to the exclusion power of the system.

D22S683 (D22) is a Class I CTR and consists of a stretch of a tandemly repeated GATA sequence followed by a stretch of TAGATA tandem repeats. Variability is present in the number of GATA repeats, as well as the number of TAGATA repeats. The additional level of complexity of this locus probably accounts for its high degree of heterozygosity (83.5%–92.9%).

These complex loci are referred to as "complex tandem repeats" (CTR) herein, and present a new type of loci particularly beneficial in DNA typing. The higher degree of variability within CTR loci is reflected by higher heterozygosity in the population. Multiplex amplification of these loci produces a higher exclusion power than those of conventional STR loci.

Prior to the present invention, CTR loci were not generally recognized as being particularly beneficial for use in DNA typing analyses. A single CTR locus, the SE33 or ACTBP2 locus, has commonly been used in forensic analysis and known to have sequence complexity and a high degree of heterozygosity (96% in Swedes). According to the definitions used herein, the SE33 locus is a Class II CTR (Moller, A., Brinkmann, B., Sequencing Data Reveal Considerable Polymorphism, Int. J. Legal Med., 106(5):262–7 (1994); Holgerson, S. et al., Fluorescent-Based Typing of the Two Short Tandem Repeat Loci HUMTH01 and HUMACTBP2: Reproducibility of Size Measurements and Genetic Variation in the Swedish Population, Electrophoresis, 15(7):890–5 (1994)). Further, although it was previously recognized that simple STR systems are readily amenable to multiplex PCR, more complex sequences presented difficulties in analysis (Kimptom, C. et al., Report on the Second EDNAP Collaborative STR Exercise, Forensic Sci. Int., 71(2):137–52 (1995)).

The methods described herein may be used in a variety of applications including, but not limited to, parentage testing, determination of tissue or sample origin, genetic relatedness studies, genetic mapping, zygosity testing in twins, evaluation of bone marrow transplantations and quality control of cultured cells. The methods may also be used in a plurality of forensic applications, such as, for example, identification of degraded or minute samples and analysis of mixed samples, such as those commonly associated with rape cases.

Generally, for the methods of the present invention, suitable template DNA may be genomic DNA, or any DNA sufficiently intact to provide at least one DNA molecule containing an intact locus of interest. RNA samples that contain the locus of interest may also be amplified by first converting the RNA to cDNA by any of the techniques well known to those of skill in the art. Although the embodiments described herein employ human genomic DNA as template DNA, it is possible that complex tandem repeats from other species will be found, or that the complex tandem repeats or their flanking sequences might be conserved between species. Thus, the method of DNA typing described herein is not restricted to human applications, but may be used in applications relating to plants and animals, such as, for example, breeding and pedigree analyses.

Any suitable amplification procedure known to those skilled in the art may be used in the present invention, including, but not limited to, polymerase chain reaction (PCR), Qβ replication, isothermal sequence replication, or ligase chain reaction. However, PCR is the preferred amplification method of the present invention. The PCR reactions components of the present invention include, but are not limited to, template DNA, reaction buffer, magnesium, locus-specific primers and DNA polymerase.

PCR reactions useful in the present invention comprise triphasic cycles wherein the total number of triphasic cycles ranges from about 10–40 cycles. Preferably, PCR reactions of the present invention comprise 15–35 triphasic cycles, more preferably, 20–33 cycles and even more preferably 25–30 triphasic cycles. Each triphasic cycle of the PCR includes a first temperature step ranging from about 90° C.–98° C. for a time period ranging from about 20 seconds to about 5 minutes, a second temperature step ranging from about 40° C.–65° C. for a time period ranging from about 20 seconds to about 5 minutes, and a third temperature step ranging from about 60° C.–77° C. for a time period ranging from about 20 seconds to about 10 minutes. Preferably, the first temperature step ranges from about 92° C.–97° C. for a time period ranging from about 30 seconds to about 3 minutes, the second temperature step ranges from about 45° C.–63° C. for a time period ranging from about 30 seconds to about 3 minutes, and the third temperature step ranges from about 65° C.–75° C. for a time period ranging from about 30 seconds to about 7 minutes. Even more preferably, the first temperature step ranges from about 93° C.–96° C. for a time period ranging from about 40 seconds to about 2 minutes, the second temperature step ranges from about 50° C.–60° C. for a time period ranging from about 40 seconds to about 2 minutes, and the third temperature step ranges from about 67° C.–73° C. for a time period ranging from about 40 seconds to about 2 minutes. In a particularly preferred embodiment, the triphasic cycles comprise a first temperature of 95° C. for 45 seconds, a second temperature of 59° C. for 45 seconds, and a third temperature of about 72° C. for about 45 seconds;

Multiplex amplifying reactions of the present invention may comprise a heating step prior to the triphasic cycling step. The temperature of the heating step may range from about 90° C.–98° C., preferably 92° C.–96° C., and most preferably 94° C.–95° C., and is for a period of time ranging from about 1–20 minutes, preferably 5–15 minutes, and even more preferably 7–12 minutes. The multiplex amplifying reactions may further comprise a holding step after the PCR cycling step. The temperature of the holding step may range from about 60° C.–80° C., preferably 65° C.–75° C., and even more preferably 68° C.–74° C., and is carried out for a period of time ranging from about 2–20 minutes, preferably 3–15 minutes and most preferably 5–10 minutes. The multiplex amplifying reaction may be cooled and stored at a temperature ranging from 4° C.–15° C. for a period of time greater than 5 minutes, or analyzed immediately. In a particularly preferred embodiment, the multiplex amplifying conditions of the present invention comprise an initial heating step at 95° C. for 10 minutes, 28 triphasic PCR cycles wherein each triphasic cycle includes a first phase of 95° C. for 45 seconds, a second phase of about 59° C. for 45 seconds and a third phase of about 72° C. for 45 seconds, a holding step of 72° C. for 7 minutes and a final cooling step at 4° C.

Multiplex amplification requires loci-specific reaction conditions and procedures. In general, optimization of multiplex amplification may be achieved through systematic variation of each reaction parameter. A Taguchi array (statistical means of minimizing the number of samples required to systematically vary each parameter of an experiment) may be used to minimize the number of variants that must be tested to achieve optimization (Taguchi G., *Reports Statist. Appl. Res.* 7:1 (1960)). The multiplexed loci of the present invention behave in a unique and unusual fashion with respect to certain parameters, such as annealing temperature, and optimization of these parameters is described in more detail in Example 3.

The methods of the present invention provide a significant improvement in exclusion power over the presently used and commercially available STR multiplexes. All other STR triplexes and quadriplexes currently used for paternity analysis have exclusion powers ranging from about 85% to about 91% (e.g., HUMF13AO1/HUMFESFPS/HUMCYARO4/HUMLIPOL,HUMCSFIPO/HUMTH01/HUMPLAZA1, and HUMHPRTB/HUMFABP/HUMCD4).

Referring to FIG. 1, use of the D9S302, D22S683, D18S535 genetic systems (indicated as Multiplex 5) of the present invention gives a power of exclusion (POE) of 98.99% for African Americans and when combined with the D3S2387/D4S2366/D5S1719/D7S1804/CSFIPO/FESFPS/TH01/LIPOL genetic systems, the multiplex has a POE of 99.99% for African Americans, which is significantly higher than any other STR triplex currently available. FIG. 1 shows the POE resulting from use of the D9S302, D22S683, D18S535 (Multiplex 5) combination of genetic systems, the D3S2387, D4S2366, D5S1719, D7S1804 (Multiplex 6) combination of genetic systems, the CSFIPO, FESFPS, TH01, LIPOL (Multiplex 8) combination of genetic systems, as well as the combination of Multiplex 5, 6 and 8 genetic systems, for the Caucasian, Black, Hispanic, Asian and Japanese races.

Referring to FIG. 1, the STR systems are grouped by multiplex as they are preferably combined. For example, D9S302, D22S683, and D18S535, referred to as Multiplex 5 (MP5), preferably has forward primers that are labeled with the ABI dye FAM. D7S1804, D3S2387, D4S2366, and D5S1719 are referred to as Multiplex 6 (MP6) and are labeled with HEX. CSFIPO, FESFPS, TH01, and LIPOL are referred to as Multiplex 8 (MP8) and are labeled with TET. Multiplexes are assembled paying close attention to size range of amplified products. It is important to make sure that the amplified fragments produced by multiplex amplifying the different STR systems that are labeled with the same dye do not overlap in size. The ABI format used in the present invention utilizes four different dyes and one TAMRA dye is used for an internal fragment size standard. A particularly preferred embodiment of the present invention is a combination (actually an undecaplex) of MP5, MP6, and MP8 amplified together in one tube.

The data shown in FIG. 1 is used to determine the theoretical power of each STR system for use in paternity testing. Additionally, it is important to determine the power of exclusion of the systems that are used together as a testing battery. The power of exclusion of a genetic system for use in paternity analysis reflects the ability of the system to exclude non-fathers (i.e., falsely accused men). A global assessment of this power of exclusion can be made using the logic that follows (note that this exclusion power varies in different racial groups). The more polymorphic a system is in any population, the more one would expect to see heterozygotes rather than homozygotes. If A=power of exclusion, H=frequency of homozygotes in a population, and h=frequency of heterozygotes in a population (note: h=1−H), the power of exclusion for a genetic system can be determined using the formula $A=h^2 (1-2 hH^2)$ (Brenner, C. & Morris, J. W., Paternity Index Calculations in Single Locus Hyper-Variable DNA Probes: Validation and Other Studies, Proceedings for The International Symposium on Human Identification, pp. 21–76 (1989)). Since the Hardy-Weinberg equilibrium formula for gene frequencies states that the frequency of individuals homozygous for an allele is the square of the gene frequency for that allele, the overall level of homozygosity for a genetic system can be determined by squaring the frequency of each allele in a population and summing those squares. The heterozygosity level is determined by subtracting that sum of squares from 1. The random man not excluded (RMNE) value represents the proportion of falsely accused men who are not excluded by the particular genetic system(s). The RMNE value is obtained by subtracting the POE value (i.e., A) from 1. To obtain an estimate of exclusion power for several genetic systems, the RMNEs from all the systems are multiplied together and subtracted from 1. Using this technique, the proportion of falsely accused men that would not be excluded after running all those particular genetic systems can be calculated, and subtracting this value from 1 produces the proportion that would be excluded (POE).

In FIG. 1, these values are listed by race for individual systems as well as multiplexes of systems. To calculate how powerful the combination of MP5 and MP6 is in Blacks, 0.0101 is multiplied by 0.0041 and the value is subtracted from 1. Thus, a testing battery that includes the loci of MP5 and MP6 as a multiplex process produces an exclusion probability of 0.99996 or 99.996%. This is a very high exclusion power for the number of combined STRs of MP5 and MP6 (seven STRs total). If MP8 is added to those two multiplexes to produce Identiplex (eleven STRs total), the exclusion power becomes 99.9998%.

The present study confirmed that not all loci are equally amenable to multiplex amplification. For example, certain GGAA repeats were impossible to amplify cleanly without the production of numerous artifactual bands, presumably due to polymerase slippage or non-specific primer annealing during the amplification process. In the present study, attempts to perform multiplex amplification using the loci D20S470, D3S2387, and D14S617 as a triplex, or D20S470, D4S243 1, D3S23 87 and D14S617, as a quadriple unsuccessful. Altering amplification parameters such as template DNA concentration, $MgCl_2$ concentration, and primer concentrations did not improve the reaction specificity or robustness of the reaction. Other loci tested for use in multiplex amplification that also failed to have reliability were D1S1656 and D1S1612. Numerous attempts to optimize the multiplex amplification for these loci resulted in failure and these loci were eventually abandoned as multiplex candidates.

In contrast, using the methods of the present invention, it is possible to obtain very clean and reproducible results for the co-amplification of complex GATA repeats. Additional CTRs based on variations of the GATA repeat can be successfully used in the system of the present invention. These complex GATA repeats and GATA variants include, but are not limited to, D9S302, D18S535, D22S683, D3S2387 (GenBank Accession No. G08236), D4S2366 (GenBank Accession No. G08339), D5S1719 (GenBank Accession No. G09994) and D7S1804 (GenBank Accession No. G08619).

Contrary to standard teaching in the art, it is not necessary that the primers used in the present invention be of approximately equivalent GC content. Primers having GC content ranging from 22% to 60% (i.e., SEQ ID NOS: 1–14) will function together in a plurality of combinations to provide a clean multiplex amplification. The primers used for the methods of the present invention may be labeled to simplify visualization, detection and analysis of the resulting amplification products. The label may be any radioactive or non-radioactive label known to those skilled in the art and may include, for example, dyes, isotopes and enzymes. In a preferred embodiment of the invention, the primers used are 5' labeled with a fluorescent label. In a particularly preferred embodiment, the primers used to multiplex amplify the D9S302, D22S683 and D18S535 loci are 5' labeled with ABI FAM (Applied Biosystems), those used to amplify the D3S2387, D4S2366, D5S1719 and D7S1804 loci are labeled with ABI HEX (Applied Biosystems) and those used to amplify the CSFIPO, FESFPS, TH01 and LIPOL loci are labeled with the fluorescent dye ABI TET (Applied Biosystems).

Contrary to expectation, when attempting to optimize the multiplex amplification of the present invention, raising the annealing temperature increased, rather than decreased, the level of spurious band formation. This is perhaps due to improper priming of DNA polymerase at the slightly higher temperatures.

Accurate titration of the multiplex reaction components greatly improves the quality of the methods of the present invention. Specifically, accurate titration of the amount of the components magnesium ($Mg^{++}$) and template DNA greatly improves the present multiplex reaction. The parameters of these two components are critical for achieving high quality amplification. For the methods of the present invention, preferably the template DNA concentration is about 0.5 to 1.5 ng/$\mu$l, the magnesium concentration is about 1.0 to 3.0 mM, primer concentrations are about 0.1 to 1.5 $\mu$M for SEQ. ID. NOS. 1, 2, 3, 4, 5, 6, 7, 8, 9, 10, 11, 12, 13 and 14, Amplitaq Gold DNA Polymerase (PE Biosystems) concentration is at about 1.0 to 5.0 units per 25 $\mu$l reaction and dNTPs are at a concentration ranging from about 150 $\mu$M to 1 mM. Most preferably, the DNA concentration is about 1.0 ng/$\mu$l, magnesium concentration is about 2.5 mM, the primers are at a concentration of about 0.2 $\mu$M each for SEQ. ID. NOS. 5, 6, 11 and 12, about 0.5 $\mu$M each for SEQ. ID. NOS. 1 and 2, about 1.0 $\mu$M each for SEQ ID NOS: 3, 4, 9, 10, 13 and 14, and 1.5 $\mu$M each for SEQ ID NOS: 7 and 8, Amplitaq Gold is at a concentration of 0.1 units/$\mu$l and dNTPs are at a concentration of 400 $\mu$M. Additional parameters and parameter conditions necessary for high quality amplification using the multiplex of the present invention include, for example, a primer annealing temperature of about 55–60° C. and a reaction volume of about 20–30 $\mu$l. In a preferred embodiment, the primer annealing temperature is about 5 9° C., the reaction volume is about 25 $\mu$l and the primer concentrations are about 0.1 to 1.5 $\mu$M. In a more preferred embodiment, primer concentrations are 0.2 $\mu$M for SEQ ID NOS: 5, 6, 11 and 12, 0.5 $\mu$M for SEQ ID NOS: 1 and 2, 1.0 $\mu$M for SEQ ID NOS: 3, 4, 9, 10, 13 and 14 and 1.5 $\mu$M for SEQ ID NOS: 7 and 8. Preferred PCR reaction conditions comprise a first heating step of about 95° C. for about 10 minutes followed by a cycling step comprising 28 triphasic cycles, each cycle consisting of a first phase of 95° C. for about 45 seconds, a second phase of about 59° C. for about 45 seconds and a third phase of about 72° C. for about 45 seconds, a second heating step of about 72° C. for about 7 minutes and a holding or cooling step of about 4° C. Unlike many, if not all, previous attempts to amplify DNA using multiplex STRs, the system described herein provides very clean results and produces only the fragments of interest. No significant spurious bands are formed, allowing for simple and accurate genotyping.

The multiplex amplifying methods of the present invention comprise at least two primers selected from the group consisting of SEQ ID NOS: 1–14 and combinations thereof. The primers used in the present invention may be locus-specific primers. In a preferred embodiment the primers used in multiplex amplifying are SEQ ID NOS: 1 and 2 for D18S535, SEQ ID NOS: 3 and 4 for D22S683, SEQ ID NOS: 5 and 6 for D9S302, SEQ ID NOS: 7 and 8 for D3S2387, SEQ ID NOS: 9 and 10 for D4S2366, SEQ ID NOS: 11 and 12 for D5S1719 and SEQ ID NOS: 13 and 14 for D7S1804.

One purpose of using multiplex amplification is to determine the genotype of a DNA sample in a typing analysis. The genotype can be described in a plurality of ways, such as, for example, the sizes of amplified fragments, the number of tandem GATA repeats, or number of GATA equivalents if the population variability is caused by complex GATA repeats.

The sequence heterogeneity of loci may be detected in a plurality of ways. In the system of the present invention, it is technically very simple to determine the genotype according to the size of the amplified repeat, as demonstrated in the examples herein. The fragments are separated by polyacrylamide gel electrophoresis, the gel stained with $AgNO_3$, and the fragment sizes determined by comparison to standards. The DNA may be visualized in a number of ways, including, but not limited to, radiolabeling, fluorescent labeling, color staining, and chemiluminescent detection.

In order to determine genotype by size using multiplex amplification, it is necessary to choose primers that yield a series of non-overlapping fragments for the multiplex loci. The oligonucleotide primers flanking the loci of the present invention were developed by researchers at the CHLC and the sequences were obtained from the GenBank. It will be appreciated by those of ordinary skill in the art that the primers defining these polymorphic microsatellites can be manipulated to change either the reaction conditions and/or the size of the fragments amplified.

There are many additional procedures that may be used to determine the genotype of the amplified locus, including, but not limited to, sequencing of the fragment, allele-specific oligonucleotide (ASO) hybridization, and capillary electrophoresis.

The multiplex of the present invention has an extremely high power of individualization in the four major racial groups. The loci of the present invention co-amplify cleanly and robustly, enabling accurate genotyping of the loci while using very small quantities of DNA. Paternity testing employing the present invention has the power to exclude 99.9998% of falsely accused African American men. The methods of the present invention greatly reduce the technical labor required in human identification analyses and, at the same time, significantly increases the reliability of the analysis.

Another embodiment of the invention is directed to an allelic ladder useful in DNA typing. The ladder may comprise at least 4 alleles from at least one locus. The at least one locus may be selected from the group of loci consisting of D9S302, D18S535, D22S683, D3S2387, D4S2366, D5S1719 and D7S1804. In a particularily preferred embodiment, the ladder comprises at least 10 alleles from the D9S302 locus, at least 5 alleles from the D18S535 locus, at least 7 alleles from the D22S683 locus, at least 6 alleles from the D3S2387 locus, at least 4 alleles from the D4S2366 locus, at least 4 alleles from the D5S1719 locus and at least 7 alleles from the D7S1804 locus. Allelic ladders of the present invention may be useful for the analysis of unknown samples. Bands in allelic ladder constructions may be spaced one full GATA (or GATA equivalent) repeat apart to be used in genotyping by comparing gel migration of these known fragments with that of specimens of unknown genotype.

Another embodiment of the invention is directed to a composition comprising a plurality of amplified loci wherein at least two of said plurality are selected from the group consisting of D9S302, D22S683, D18S535. The plurality may further comprise the D3S2387, D4S2366, D5S1719 and D7S1804 genetic systems or loci. In a preferred embodiment, the plurality of loci of the composition comprises each of the D9S302, D22S683, D18S535, D3S2387, D4S2366, D5S1719 and D7S1804 loci.

Another embodiment of the present invention is directed to a kit for multiplex amplifying DNA comprising a plurality of loci, wherein at least one of said plurality of loci is selected from the group consisting of D3S2387, D4S2366, D5S1719 and D7S1804. The plurality may further comprise at least one locus selected from the group consisting of D9S302, D22S683, D18S535 and at least one locus selected from the group consisting of CSFIPO, FESFPS, TH01 and LIPOL. In a preferred embodiment, the system comprises multiplex amplifying each of the D3S2387, D4S2366, D5S1719, D7S1804, D9S302, D22S683, D18S535, CSFIPO, FESFPS, TH01 and LIPOL loci of DNA.

The ladders, kits and compositions of the present invention may be used in a variety of applications including, but not limited to, parentage testing, determination of tissue or sample origin, genetic relatedness studies, genetic mapping, zygosity testing in twins, evaluation of bone marrow transplantations and quality control of cultured cells. The ladders, kits and compositions may also be used in a plurality of forensic applications, such as, for example, identification of degraded or minute samples and analysis of mixed samples, such as those commonly associated with rape cases.

The following examples serve to illustrate specific embodiments of the invention, but should not be considered as a limitation on the scope of the invention.

EXAMPLES

Example 1

Polymorphic Loci

The loci of the present invention and primers suitable for their amplification are as follows:

D18S535

The chromosomal location of D18S535 is 18q12.2–12.3. The forward primer is 20 nucleotides long, and its sequence is: 5'TCATGTGACAAAAGCCACAC3'(SEQ ID NO: 1). The reverse primer is 25 nucleotides long, and its sequence is: 5'AGACAGAAATATAGATGAGAATGCA3'(SEQ ID NO: 2). The size range of fragments found in over 800 humans is 122 to 158 base pairs.

D22S683

D22S683 has been localized only to chromosome 22. The forward primer is 23 nucleotides long, and its sequence is: 5'AACAAAACAAAACAAAACAAACA3'(SEQ ID NO: 3). The reverse primer is 20 nucleotides long, and its sequence is: 5'GGTGGAAATGCCTCATGTAG3'(SEQ ID NO: 4). The size range of fragments found in over 800 humans is 162 to 226 base pairs.

D9S302

The chromosomal location of D9S302 is 9q31–q33. The primers used in the amplification reaction are each 20 nucleotides long. The sequence of the forward primer is: 5'GGGGACAGACTCCAGATACC3'(SEQ ID NO: 5) and the sequence of the reverse primer is: 5'GCGACAGAGTGAAACCTTGT3'(SEQ ID NO: 6). The size range of fragments found in over 800 humans is 236 to 364 base pairs.

D3S2387

D3S2387 has been localized to chromosome 3. The primers used in the amplification reaction are each 20 nucleotides long. The sequence of the forward primer is: 5'AAA GCT AGA AGG AGC TGG CT3'(SEQ ID NO: 7) and the sequence of the reverse primer is: 5'GGG TGA CAG AGT GAG ATG TG 3'(SEQ ID NO: 8). The size range of fragments found in over 750 humans is 164 to 228 base pairs.

D4S2366

D4S2366 has been localized to chromosome 4. The primers used in the amplification reaction are each 20 nucleotides long. The sequence of the forward primer is: 5'TCC TGA CAT TCC TAG GGT GA 3"(SEQ ID NO: 9) and the sequence of the reverse primer is: 5'AAA ACA AAT ATG GCT CTA TCT ATC G 3'(SEQ ID NO: 10). The size range of fragments found in over 750 humans is 113 to 160 base pairs.

D5S1719

D5S1719 has been localized to chromosome 5. The primers used in the amplification reaction are each 20 nucleotides long. The sequence of the forward primer is: 5'GTT CAT TTA GAG TAA CAG GGC C 3'(SEQ ID NO: 11) and the sequence of the reverse primer is: 5'ATG GCA GAT TGT GGG ACT TA 3'(SEQ ID NO: 12). The size range of fragments found in over 750 humans is 79 to 112 base pairs.

D7S1804

D7S1804 has been localized to chromosome 7. The primers used in the amplification reaction are each 20 nucleotides long. The sequence of the forward primer is: 5'TTC AAG TGG TTG GGT TCA CT 3'(SEQ ID NO: 13) and the sequence of the reverse primer is: 5'TGG GTC TAG TCC AGT GGT GT 3'(SEQ ID NO: 14). The size range of fragments found in over 750 humans is 235 to 300 base pairs.

Example 2

Multiplex PCR

Five to twenty nanograms of genomic DNA were amplified in a Perkin Elmer 9600 thermal cycler in a 25 $\mu$l reaction. The other components of each reaction were 10 mM Tris-HCl, pH 8.3; 50 mM KCl; 2.5 mM MgCl$_2$; 0.01% gelatin; 400 $\mu$M of each deoxynucleoside triphosphate; 2.25 Units of AmpliTaq Gold DNA Polymerase.

Primer concentrations were arbitrarily determined at 20 pmol per reaction.

Comparing the intensity of each locus on ABI 377 sequencing gels enabled the determination of optimal primer concentrations. The optimal primer concentrations were a concentration of about 0.2 $\mu$M each for SEQ. ID. NOS: 5, 6, 11 and 12, about 0.5 $\mu$M each for SEQ. ID. NOS: 1 and 2, about 1.0 $\mu$M each for SEQ ID NOS: 3,4, 9, 10, 13 and 14, and 1.5 $\mu$M each for SEQ ID NOS: 7 and 8.

The PCR conditions for this multiplex were an initial hold at 95° C. for 10 minutes; 28 cycles of 95° C. for 45 seconds, 59° C. for 45 seconds, and 72° C. for 45 sec a hold of 72° C. for 7 minutes; and a final hold at 4° C.

Example 3

Determining CTR Genotypes and Population Variability

Genotypic variation at seven loci embodied by this invention (D9, D22, D18, D3, D4, D5 and D7) in five major racial groups (Caucasian, Black, Hispanic, Asian and Japanese) was determined by analysis on an ABI Prism 377 DNA sequencer (Applied Biosystems) using the Genescan software package. The results are shown in Tables 1–7. 0.5 μl of amplified multiplex products mixed with ABI size standard and loading buffer were electrophoresed through a 4%/1× TBE denaturing polyacrylamide gel (19:1 acrylamide:bisacrylamide, 7.5 M urea) for 2.5 hours at 3.0 kV constant voltage. Next, fluorescently labeled fragments were detected and scored by Genescan software. GATA equivalents (repeat numbers) were determined by sequencing different sized amplified products for each system. The conditions for sequencing reactions are described below, in Example 4.

The African American and Caucasian specimens used in the databasing were parents from paternity analyses previously performed in this laboratory. Only unrelated specimens were used. Blood specimens from Asians and Hispanics were obtained from the Houston Blood Center. Approximately 200–400 alleles/samples of each race were amplified and analyzed.

TABLE 1

LOCUS: D9S302
N = 19886 7998 3462 498 1486

| ALLELE | Caucasian Frequency | Black Frequency | Hispanic Frequency | Asian Frequency | Asian/Japanese Frequency |
|---|---|---|---|---|---|
| <27 | 0.0003 | 0.0001 | 0.0003 | 0.002 | 0.002 |
| 27 | 0.00639 | 0.0016 | 0.0052 | 0.002 | |
| 27.1 | | | | | |
| 27.2 | | | | | |
| 27.3 | | | | | |
| 28 | 0.00176 | 0.0019 | 0.0003 | | |
| 28.1 | | | | | |
| 28.2 | | | | | |
| 28.3 | | | | | |
| 29 | 0.00608 | 0.0158 | 0.0075 | 0.002 | |
| 29.1 | | | | | |
| 29.2 | 0.00005 | | | | |
| 29.3 | | | | | |
| 30 | 0.07035 | 0.0256 | 0.0381 | 0.01 | 0.0054 |
| 30.1 | | | | | |
| 30.2 | 0.00015 | 0.001 | | | |
| 30.3 | | | | | |
| 31 | 0.14447 | 0.0475 | 0.0919 | 0.0482 | 0.041 |
| 31.1 | | | | | |
| 31.2 | 0.00055 | 0.0005 | 0.0003 | 0.002 | |
| 31.3 | | | | | |
| 32 | 0.16544 | 0.0905 | 0.1586 | 0.0803 | 0.0363 |
| 32.1 | | | | | |
| 32.2 | 0.0002 | 0.0018 | | 0.002 | 0.0047 |
| 32.3 | | | | | |
| 33 | 0.13934 | 0.0428 | 0.1476 | 0.0723 | 0.0262 |
| 33.1 | | | | | |
| 33.2 | 0.00025 | 0.0213 | 0.0017 | 0.002 | 0.0047 |
| 33.3 | | | | | |
| 34 | 0.04828 | 0.0143 | 0.0479 | 0.0281 | 0.0094 |
| 34.1 | | | | | |
| 34.2 | 0.00191 | 0.0286 | 0.0061 | 0.006 | 0.0162 |
| 34.3 | | | | | |
| 35 | 0.00905 | 0.0039 | 0.0078 | 0.006 | 0.0007 |
| 35.1 | | | | | |
| 35.2 | 0.00513 | 0.0235 | 0.013 | 0.0301 | 0.0545 |
| 35.3 | | | | | |
| 36 | 0.01091 | 0.0058 | 0.0078 | | 0.0007 |
| 36.1 | | | | | |
| 36.2 | 0.01443 | 0.0384 | 0.0422 | 0.1104 | 0.105 |
| 36.3 | | | | | |
| 37 | 0.01599 | 0.006 | 0.011 | | 0.0013 |
| 37.1 | | | | | |
| 37.2 | 0.04908 | 0.0801 | 0.0696 | 0.0984 | 0.1454 |
| 37.3 | | | | | |
| 38 | 0.01398 | 0.0048 | 0.009 | 0.004 | 0.0013 |
| 38.1 | | | | | |

TABLE 1-continued

LOCUS: D9S302
N = 19886 7998 3462 498 1486

| ALLELE | Caucasian Frequency | Black Frequency | Hispanic Frequency | Asian Frequency | Asian/Japanese Frequency |
|---|---|---|---|---|---|
| 38.2 | 0.05547 | 0.1173 | 0.0745 | 0.1084 | 0.1487 |
| 38.3 | | | | | |
| 39 | 0.00613 | 0.0065 | 0.0055 | | 0.0034 |
| 39.1 | | | | | |
| 39.2 | 0.06155 | 0.1495 | 0.0789 | 0.1365 | 0.142 |
| 39.3 | | | | | |
| 40 | 0.00297 | 0.0024 | 0.0035 | 0.002 | 0.0007 |
| 40.1 | | | | | |
| 40.2 | 0.05592 | 0.1138 | 0.0705 | 0.0843 | 0.1023 |
| 40.3 | | | | | |
| 41 | 0.00106 | 0.0009 | 0.0003 | 0.0141 | 0.004 |
| 41.1 | | | | | |
| 41.2 | 0.04958 | 0.0773 | 0.05 | 0.0663 | 0.0518 |
| 41.3 | | | | | |
| 42 | 0.0004 | 0.0005 | 0.0009 | 0.012 | 0.0074 |
| 42.1 | | | | | |
| 42.2 | 0.03243 | 0.0443 | 0.028 | 0.0382 | 0.0525 |
| 42.3 | | | | | |
| 43 | 0.00116 | 0.0008 | 0.0006 | 0.006 | 0.0034 |
| 43.1 | | | | | |
| 43.2 | 0.01287 | 0.0194 | 0.011 | 0.0201 | 0.0215 |
| 43.3 | | | | | |
| 44 | 0.0007 | 0.0004 | 0.0006 | | 0.002 |
| 44.1 | | | | | |
| 44.2 | 0.01051 | 0.0051 | 0.0064 | 0.004 | 0.0034 |
| 44.3 | | | | | |
| 45 | 0.00065 | 0.0005 | 0.0009 | | 0.0007 |
| 45.1 | | | | | |
| 45.2 | 0.00136 | 0.0005 | 0.0003 | | |
| 45.3 | | | | | |
| 46 | 0.00256 | | 0.0012 | 0.002 | 0.0007 |
| >46 | 0.00055 | 0.0054 | 0.0012 | | 0.0007 |
| TOTALS: | 0.99996 | 1.0004 | 1.0005 | 0.9997 | 1 |

TABLE 2

LOCUS: D22S683
N = 19924 7988 3476 494 1490

| ALLELE | Caucasian Frequency | Black Frequency | Hispanic Frequency | Asian Frequency | Asian/Japanese Frequency |
|---|---|---|---|---|---|
| <11 | 0.00141 | 0.0006 | 0.0017 | 0.004 | 0.0107 |
| 11 | 0.00025 | 0.0001 | 0.0003 | | 0.0007 |
| 11.1 | | | | | |
| 11.2 | 0.11042 | 0.0408 | 0.088 | 0.334 | 0.2785 |
| 11.3 | | | | | |
| 12 | 0.00231 | 0.0004 | 0.0026 | | 0.0027 |
| 12.1 | | | | | |
| 12.2 | 0.02986 | 0.0095 | 0.0207 | 0.0243 | 0.0376 |
| 12.3 | | | | | |
| 13 | 0.08723 | 0.0247 | 0.0892 | 0.0972 | 0.0604 |
| 13.1 | | 0.0001 | | | |
| 13.2 | 0.13677 | 0.1023 | 0.0811 | 0.0304 | 0.0268 |
| 13.3 | 0.00005 | | 0.0003 | | |
| 14 | 0.19098 | 0.0515 | 0.2048 | 0.17 | 0.2081 |
| 14.1 | 0.00005 | 0.0001 | | | |
| 14.2 | 0.09064 | 0.0742 | 0.1844 | 0.0587 | 0.0919 |
| 14.3 | 0.00005 | 0.0001 | 0.0003 | | |
| 15 | 0.04 | 0.0096 | 0.0391 | 0.0587 | 0.0644 |
| 15.1 | | | | | |
| 15.2 | 0.0666 | 0.0687 | 0.0567 | 0.0486 | 0.0772 |
| 15.3 | 0.0001 | 0.001 | 0.0023 | | |
| 16 | 0.00783 | 0.0109 | 0.0147 | 0.0081 | 0.0154 |
| 16.1 | 0.00005 | 0.0004 | | | |
| 16.2 | 0.05476 | 0.0463 | 0.0437 | 0.0283 | 0.0161 |
| 16.3 | 0.001 | 0.004 | 0.0029 | | 0.0007 |
| 17 | 0.00391 | 0.0228 | 0.0046 | 0.0101 | 0.006 |

TABLE 2-continued

LOCUS: D22S683
N = 19924 7988 3476 494 1490

| ALLELE | Caucasian Frequency | Black Frequency | Hispanic Frequency | Asian Frequency | Asian/Japanese Frequency |
|---|---|---|---|---|---|
| 17.1 | 0.00015 | 0.0021 | 0.0009 | | |
| 17.2 | 0.02153 | 0.0123 | 0.0138 | 0.0061 | 0.0027 |
| 17.3 | 0.00015 | 0.001 | | | |
| 18 | 0.02771 | 0.027 | 0.0161 | 0.0121 | 0.0342 |
| 18.1 | 0.00025 | 0.0242 | 0.0023 | | |
| 18.2 | 0.00462 | 0.0158 | 0.004 | 0.002 | 0.0007 |
| 18.3 | 0.0002 | 0.0019 | | | |
| 19 | 0.07072 | 0.0347 | 0.0469 | 0.0445 | 0.0309 |
| 19.1 | 0.00025 | 0.0143 | 0.0012 | | |
| 19.2 | 0.00627 | 0.1715 | 0.0207 | 0.0081 | 0.0027 |
| 19.3 | 0.0001 | 0.008 | 0.0003 | | |
| 20 | 0.02218 | 0.0366 | 0.0219 | 0.0324 | 0.0228 |
| 20.1 | | 0.0006 | | | |
| 20.2 | 0.01169 | 0.0776 | 0.0144 | 0.0061 | 0.0034 |
| 20.3 | | 0.0006 | 0.0003 | | |
| 21 | 0.00241 | 0.0283 | 0.0043 | 0.0081 | 0.0034 |
| 21.1 | | | 0.0003 | | |
| 21.2 | 0.0013 | 0.02 | 0.0032 | 0.002 | 0.0013 |
| 21.3 | | 0.0001 | | | |
| 22 | 0.00452 | 0.0333 | 0.0069 | 0.0061 | |
| 22.1 | | | | | |
| 22.2 | 0.00025 | 0.0106 | 0.0006 | | |
| 22.3 | | | | | |
| 23 | 0.0009 | 0.0034 | 0.0017 | | |
| >23 | 0.0005 | 0.0079 | 0.0029 | | 0.0007 |
| TOTALS: | 0.99997 | 0.9999 | 1.0001 | 0.9999 | 1 |

TABLE 3

LOCUS: D18S535
N = 19952 8034 3486 494 1498

| ALLELE | Caucasian Frequency | Black Frequency | Hispanic Frequency | Asian Frequency | Asian/Japanese Frequency |
|---|---|---|---|---|---|
| >7 | | | | | |
| 7 | 0.0002 | | | | |
| 8 | 0.0001 | 0.0021 | | | |
| 9 | 0.09287 | 0.0203 | 0.0473 | 0.2368 | 0.2303 |
| 10 | 0.00782 | 0.0249 | 0.0055 | 0.0304 | 0.022 |
| 11 | 0.01739 | 0.1085 | 0.0186 | 0.0121 | 0.0127 |
| 12 | 0.19838 | 0.2303 | 0.2034 | 0.1437 | 0.1188 |
| 13 | 0.33084 | 0.2844 | 0.3092 | 0.2227 | 0.2844 |
| 13.3 | 0.00005 | | | | |
| 14 | 0.24173 | 0.2435 | 0.2923 | 0.2753 | 0.233 |
| 15 | 0.10139 | 0.0783 | 0.115 | 0.0688 | 0.0881 |
| 16 | 0.00852 | 0.0075 | 0.0083 | 0.0101 | 0.0107 |
| >16 | 0.0007 | 0.0002 | 0.0003 | | |
| TOTALS: | 0.99999 | 0.9998 | 0.9996 | 0.9999 | 1 |

TABLE 4

LOCUS: D3S2387
N = 370 396 366 248 298

| ALLELE | Caucasian Frequency | Black Frequency | Hispanic Frequency | Asian Frequency | Asian/Japanese Frequency |
|---|---|---|---|---|---|
| <20 | 0 | 0 | 0 | 0 | 0 |
| 20 | 0 | 0.0051 | 0 | 0 | 0 |
| 20.1 | 0 | 0 | 0 | 0 | 0 |
| 20.2 | 0 | 0.0758 | 0 | 0 | 0 |
| 20.3 | 0 | 0 | 0 | 0 | 0 |
| 21 | 0 | 0.0051 | 0.0164 | 0.0202 | 0.0101 |
| 21.1 | 0 | 0 | 0 | 0 | 0 |
| 21.2 | 0 | 0.0025 | 0 | 0 | 0 |
| 21.3 | 0 | 0 | 0 | 0 | 0 |
| 22 | 0.0757 | 0.053 | 0.2049 | 0.1613 | 0.1846 |
| 22.1 | 0 | 0 | 0 | 0 | 0 |
| 22.2 | 0 | 0 | 0 | 0 | 0 |
| 22.3 | 0 | 0 | 0 | 0 | 0 |
| 23 | 0.0378 | 0.0909 | 0.0574 | 0.0847 | 0.104 |
| 23.1 | 0 | 0 | 0 | 0 | 0 |
| 23.2 | 0 | 0.0126 | 0.0027 | 0 | 0 |
| 23.3 | 0 | 0 | 0 | 0 | 0 |
| 24 | 0.0676 | 0.1061 | 0.1339 | 0.0766 | 0.0638 |
| 24.1 | 0 | 0 | 0 | 0 | 0 |
| 24.2 | 0 | 0.0101 | 0.0027 | 0 | 0 |
| 24.3 | 0 | 0 | 0 | 0 | 0 |
| 25 | 0.0811 | 0.1414 | 0.082 | 0.0927 | 0.1443 |
| 25.1 | 0 | 0 | 0 | 0 | 0 |
| 25.2 | 0 | 0.048 | 0 | 0.004 | 0 |
| 25.3 | 0 | 0 | 0 | 0 | 0 |
| 26 | 0.1676 | 0.0934 | 0.123 | 0.1855 | 0.2416 |
| 26.1 | 0 | 0 | 0 | 0 | 0 |
| 26.2 | 0 | 0.0606 | 0.0027 | 0.004 | 0.0034 |
| 26.3 | 0 | 0 | 0 | 0 | 0 |
| 27 | 0.1919 | 0.0909 | 0.1393 | 0.1734 | 0.1309 |
| 27.1 | 0 | 0 | 0 | 0 | 0 |
| 27.2 | 0.0027 | 0.0253 | 0.0082 | 0.004 | 0.0034 |
| 27.3 | 0 | 0 | 0 | 0 | 0 |
| 28 | 0.2162 | 0.0606 | 0.1148 | 0.1089 | 0.0671 |
| 28.1 | 0 | 0 | 0 | 0 | 0 |
| 28.2 | 0.0027 | 0.0556 | 0.0055 | 0 | 0.0067 |
| 28.3 | 0 | 0 | 0 | 0 | 0 |
| 29 | 0.1162 | 0.0227 | 0.0601 | 0.0645 | 0.0235 |
| 29.1 | 0 | 0 | 0 | 0 | 0 |
| 29.2 | 0 | 0.0076 | 0.0027 | 0 | 0 |
| 29.3 | 0 | 0 | 0 | 0 | 0 |
| 30 | 0.0189 | 0.0253 | 0.0246 | 0.0202 | 0.0168 |
| 30.1 | 0 | 0 | 0 | 0 | 0 |
| 30.2 | 0 | 0.0025 | 0.0109 | 0 | 0 |
| 30.3 | 0 | 0 | 0 | 0 | 0 |
| 31 | 0.0108 | 0.0051 | 0.0082 | 0 | 0 |
| 31.1 | 0 | 0 | 0 | 0 | 0 |
| 31.2 | 0 | 0 | 0 | 0 | 0 |
| 31.3 | 0 | 0 | 0 | 0 | 0 |
| 32 | 0.0108 | 0 | 0 | 0 | 0 |
| 32.1 | 0 | 0 | 0 | 0 | 0 |
| 32.2 | 0 | 0 | 0 | 0 | 0 |
| 32.3 | 0 | 0 | 0 | 0 | 0 |
| 33 | 0 | 0 | 0 | 0 | 0 |
| >33 | 0 | 0 | 0 | 0 | 0 |
| TOTALS: | 1 | 1.0002 | 1 | 1 | 1.0002 |

TABLE 5

LOCUS: D4S2366
N = 238 378 306 256 238

| ALLELE | Caucasian Frequency | Black Frequency | Hispanic Frequency | Asian Frequency | Asian/Japanese Frequency |
|---|---|---|---|---|---|
| <10 | 0 | 0 | 0 | 0.0039 | 0 |
| 10 | 00042 | 0 | 0 | 0 | 0 |
| 10.1 | 0 | 0 | 0 | 0 | 0 |
| 10.2 | 0 | 0 | 0 | 0 | 0.0042 |
| 10.3 | 0 | 0 | 0 | 0 | 0.0084 |
| 11 | 0.3445 | 0.1799 | 0.2157 | 0.3516 | 0.2605 |
| 11.1 | 0 | 0 | 0 | 0 | 0.0042 |
| 11.2 | 0.0042 | 0.0053 | 0 | 0 | 0 |
| 11.3 | 0 | 0 | 0 | 0.0039 | 0 |
| 12 | 0.1933 | 0.3783 | 0.1275 | 0.1016 | 0.021 |

TABLE 5-continued

LOCUS: D4S2366
N = 238 378 306 256 238

| ALLELE | Caucasian Frequency | Black Frequency | Hispanic Frequency | Asian Frequency | Asian/Japanese Frequency |
|---|---|---|---|---|---|
| 12.1 | 0.0042 | 0 | 0 | 0 | 0 |
| 12.2 | 0 | 0.0026 | 0 | 0 | 0 |
| 12.3 | 0 | 0 | 0 | 0.0039 | 0.0042 |
| 13 | 0.0462 | 0.1138 | 0.1405 | 0.2227 | 0.2941 |
| 13.1 | 0 | 0 | 0 | 0 | 0 |
| 13.2 | 0 | 0.0053 | 0 | 0 | 0 |
| 13.3 | 0.0042 | 0.0026 | 0 | 0.0039 | 0.0042 |
| 14 | 0.1387 | 0.2143 | 0.2124 | 0.1055 | 0.1891 |
| 14.1 | 0 | 0 | 0 | 0 | 0 |
| 14.2 | 0 | 0 | 0 | 0 | 0 |
| 14.3 | 0 | 0 | 0.0033 | 0.0039 | 0.0042 |
| 15 | 0.1807 | 0.0847 | 0.1373 | 0.082 | 0.0714 |
| 15.1 | 0 | 0 | 0 | 0 | 0.0042 |
| 15.2 | 0 | 0 | 0 | 0 | 0 |
| 15.3 | 0 | 0 | 0 | 0 | 0 |
| 16 | 0.0798 | 0.0132 | 0.1471 | 0.1055 | 0.1008 |
| 16.1 | 0 | 0 | 0.0033 | 0 | 0 |
| 16.2 | 0 | 0 | 0 | 0 | 0 |
| 16.3 | 0 | 0 | 0 | 0 | 0 |
| 17 | 0 | 0 | 0.0131 | 0.0078 | 0.0294 |
| 17.1 | 0 | 0 | 0 | 0 | 0 |
| 17.2 | 0 | 0 | 0 | 0 | 0 |
| 17.3 | 0 | 0 | 0 | 0 | 0 |
| 18 | 0 | 0 | 0 | 0 | 0 |
| 18.1 | 0 | 0 | 0 | 0.0039 | 0 |
| 18.2 | 0 | 0 | 0 | 0 | 0 |
| 18.3 | 0 | 0 | 0 | 0 | 0 |
| 19 | 0 | 0 | 0 | 0 | 0 |
| 16.1 | 0 | 0 | 0 | 0 | 0 |
| 19.2 | 0 | 0 | 0 | 0 | 0 |
| 19.3 | 0 | 0 | 0 | 0 | 0 |
| 20 | 0 | 0 | 0 | 0 | 0 |
| >20 | 0 | 0 | 0 | 0 | 0 |
| TOTALS: | 1 | 1 | 1.0002 | 1.0001 | 0.9999 |

TABLE 6

LOCUS: D5S1719
N = 388 386 210 298 300

| ALLELE | Caucasian Frequency | Black Frequency | Hispanic Frequency | Asian Frequency | Asian/Japanese Frequency |
|---|---|---|---|---|---|
| >6 | 0 | 0 | 0 | 0 | 0 |
| 6 | 0.0644 | 0.0285 | 0.081 | 0.0235 | 0.01 |
| 6.1 | 0 | 0.0026 | 0 | 0 | 0 |
| 6.2 | 0 | 0 | 0 | 0 | 0 |
| 6.3 | 0 | 0 | 0 | 0 | 0 |
| 7 | 0.2371 | 0.158 | 0.5429 | 0.3826 | 0.4933 |
| 7.1 | 0 | 0 | 0 | 0 | 0 |
| 7.2 | 0 | 0 | 0 | 0 | 0 |
| 7.3 | 0.0026 | 0 | 0 | 0 | 0 |
| 8 | 0.0103 | 0.0181 | 0.019 | 0.1342 | 0.0767 |
| 8.1 | 0 | 0 | 0.0048 | 0 | 0 |
| 8.2 | 0 | 0 | 0 | 0 | 0.01 |
| 8.3 | 0.0052 | 0.0026 | 0 | 0.0034 | 0 |
| 9 | 0.0335 | 0.0881 | 0.0286 | 0.094 | 0.11 |
| 9.1 | 0 | 0.0026 | 0 | 0 | 0 |
| 9.2 | 0 | 0 | 0 | 0 | 0 |
| 9.3 | 0.1392 | 0.215 | 0.0429 | 0.1242 | 0.0767 |
| 10 | 0.1418 | 0.0725 | 0.1143 | 0.0503 | 0.0333 |
| 10.1 | 0 | 0 | 0 | 0 | 0 |
| 10.2 | 0 | 0 | 0 | 0 | 0 |
| 10.3 | 0.1386 | 0.1503 | 0.0762 | 0.0671 | 0.0467 |
| 11 | 0.1546 | 0.0674 | 0.0667 | 0.0604 | 0.0133 |
| 11.1 | 0 | 0.0026 | 0 | 0 | 0.0033 |
| 11.2 | 0 | 0.0259 | 0 | 0 | 0.0033 |
| 11.3 | 0.067 | 0.1632 | 0.019 | 0.0604 | 0.1133 |

TABLE 6-continued

LOCUS: D5S1719
N = 388 386 210 298 300

| ALLELE | Caucasian Frequency | Black Frequency | Hispanic Frequency | Asian Frequency | Asian/Japanese Frequency |
|---|---|---|---|---|---|
| 12 | 0.0052 | 0 | 0.0048 | 0 | 0 |
| 12.1 | 0 | 0 | 0 | 0 | 0 |
| 12.2 | 0 | 0.0026 | 0 | 0 | 0.0033 |
| 12.3 | 0.0026 | 0 | 0 | 0 | 0.0067 |
| 13 | 0 | 0 | 0 | 0 | 0 |
| 13.1 | 0 | 0 | 0 | 0 | 0 |
| 13.2 | 0 | 0 | 0 | 0 | 0 |
| 13.3 | 0 | 0 | 0 | 0 | 0 |
| 14 | 0 | 0 | 0 | 0 | 0 |
| 14.1 | 0 | 0 | 0 | 0 | 0 |
| 14.2 | 0 | 0 | 0 | 0 | 0 |
| 14.3 | 0 | 0 | 0 | 0 | 0 |
| 15 | 0 | 0 | 0 | 0 | 0 |
| 15.1 | 0 | 0 | 0 | 0 | 0 |
| 15.2 | 0 | 0 | 0 | 0 | 0 |
| 15.3 | 0 | 0 | 0 | 0 | 0 |
| 16 | 0 | 0 | 0 | 0 | 0 |
| >16 | 0 | 0 | 0 | 0 | 0 |
| TOTALS: | 1.0001 | 1 | 1.0002 | 1.0001 | 0.9999 |

TABLE 7

LOCUS: D7S804
N = 340 386 368 320 336

| ALLELE | Caucasian Frequency | Black Frequency | Hispanic Frequency | Asian Frequency | Asian/Japanese Frequency |
|---|---|---|---|---|---|
| <21.2 | 0 | 0 | 0 | 0 | 0 |
| 21.2 | 0 | 0 | 0 | 0 | 0 |
| 21.3 | 0 | 0 | 0 | 0 | 0 |
| 22 | 0 | 0.0181 | 0 | 0 | 0 |
| 22.1 | 0 | 0 | 0 | 0 | 0 |
| 22.2 | 0 | 0 | 0 | 0 | 0 |
| 22.3 | 0 | 0 | 0 | 0 | 0 |
| 23 | 0.0147 | 0.0104 | 0.0136 | 0.0094 | 0 |
| 23.1 | 0 | 0 | 0 | 0 | 0 |
| 23.2 | 0 | 0 | 0 | 0 | 0 |
| 23.3 | 0 | 0 | 0 | 0 | 0 |
| 24 | 0.0206 | 0.0052 | 0.0054 | 0.0094 | 0.003 |
| 24.1 | 0 | 0 | 0 | 0 | 0 |
| 24.2 | 0 | 0.013 | 0 | 0 | 0 |
| 24.3 | 0 | 0 | 0 | 0 | 0 |
| 25 | 0.1618 | 0.0933 | 0.1522 | 0.1063 | 0.2113 |
| 25.1 | 0 | 0 | 0 | 0 | 0 |
| 25.2 | 0 | 0.0155 | 0 | 0 | 0 |
| 25.3 | 0 | 0 | 0 | 0 | 0 |
| 26 | 0.0765 | 0.0829 | 0.0353 | 0.0656 | 0.0714 |
| 26.1 | 0 | 0 | 0 | 0 | 0 |
| 26.2 | 0 | 0 | 0 | 0 | 0 |
| 26.3 | 0 | 0 | 0 | 0 | 0 |
| 27 | 0.0824 | 0.1062 | 0.1277 | 0.1531 | 0.1131 |
| 27.1 | 0 | 0 | 0 | 0 | 0 |
| 27.2 | 0 | 0 | 0 | 0 | 0 |
| 27.3 | 0 | 0 | 0 | 0 | 0 |
| 28 | 0.2059 | 0.1528 | 0.1522 | 0.1969 | 0.1369 |
| 28.1 | 0 | 0 | 0 | 0 | 0 |
| 28.2 | 0 | 0 | 0 | 0 | 0 |
| 28.3 | 0 | 0 | 0 | 0 | 0 |
| 29 | 0.1794 | 0.1166 | 0.1495 | 0.1906 | 0.131 |
| 29.1 | 0 | 0 | 0 | 0 | 0 |
| 29.2 | 0 | 0 | 0 | 0 | 0 |
| 29.3 | 0 | 0 | 0 | 0 | 0 |
| 30 | 0.0941 | 0.0544 | 0.0462 | 0.0594 | 0.0714 |
| 30.1 | 0 | 0 | 0 | 0 | 0 |
| 30.2 | 0 | 0.0078 | 0 | 0 | 0 |
| 30.3 | 0 | 0 | 0 | 0 | 0 |
| 31 | 0.0118 | 0.044 | 0.0326 | 0.075 | 0.0476 |

TABLE 7-continued

LOCUS: D7S804
N = 340 386 368 320 336

| ALLELE | Caucasian Frequency | Black Frequency | Hispanic Frequency | Asian Frequency | Asian/ Japanese Frequency |
|---|---|---|---|---|---|
| 31.1 | 0 | 0 | 0 | 0 | 0 |
| 31.2 | 0 | 0 | 0 | 0 | 0 |
| 31.3 | 0 | 0 | 0 | 0 | 0 |
| 32 | 0.0324 | 0.0907 | 0.144 | 0.0469 | 0.1071 |
| 32.1 | 0 | 0 | 0 | 0 | 0 |
| 32.2 | 0 | 0 | 0.0027 | 0 | 0 |
| 32.3 | 0 | 0 | 0 | 0 | 0 |
| 33 | 0.05 | 0.0829 | 0.0842 | 0.0375 | 0.0655 |
| 33.1 | 0 | 0 | 0 | 0 | 0 |
| 33.2 | 0 | 0 | 0 | 0 | 0 |
| 33.3 | 0 | 0 | 0 | 0 | 0 |
| 34 | 0.0294 | 0.0725 | 0.0326 | 0.0406 | 0.0268 |
| 34.1 | 0 | 0 | 0 | 0 | 0 |
| 34.2 | 0 | 0 | 0 | 0 | 0 |
| 34.3 | 0 | 0 | 0 | 0 | 0 |
| 35 | 0.0235 | 0.0233 | 0.019 | 0.0063 | 0.006 |
| 35.1 | 0 | 0 | 0 | 0 | 0 |
| 35.2 | 0 | 0 | 0 | 0 | 0 |
| 35.3 | 0 | 0 | 0 | 0 | 0 |
| 36 | 0.0118 | 0.0104 | 0.0027 | 0.0031 | 0.006 |
| 36.1 | 0 | 0 | 0 | 0 | 0 |
| 36.2 | 0 | 0 | 0 | 0 | 0 |
| 36.3 | 0 | 0 | 0 | 0 | 0 |
| 37 | 0.0059 | 0 | 0 | 0 | 0.003 |
| >37 | 0 | 0 | 0 | 0 | 0 |
| TOTALS: | 1.0002 | 1 | 0.9999 | 1.0001 | 1.0001 |

Allele calls were determined by comparing the unknown typing to Centre d'Étude Polymorphism Humane (CEPH) samples 1331–01 and 1331–02 Allele sizes for these samples were obtained from gene mapping researchers at the Cooperative Human Linkage Center (CHLC). For the population database gels, BioImage Whole Band Analysis Software was used to assist in making allele calls in base pairs since exact numbers of GATA repeats were not known at the time.

Tables 1–7 contains allele frequencies from the four major racial groups, as well as for Japanese. The frequency data for each allele is produced by dividing the number of times that allele was observed by the total number of alleles scored for that STR system. If all frequencies are summed, the sum should be equal to 1.0 but may be a bit off because of rounding errors. Allele designations are based on number of repeats (in GATA equivalents). Thus, an allele designated 30 has 30 GATA-equivalents in the amplified fragment. Alleles designated with decimal points have extra nucleotides. For example, a 37.2 allele has 37 and one-half GATA equivalents (37 full repeats plus 2 extra nucleotides, thus 37.2). If an allele is designated 9.3 it has 9 GATA equivalents plus 3 extra nucleotides.

All data for D9S302, D22S683, and D18S535 were extracted from our databases using samples we have run in paternity cases. The data for D7S1804, D3S2387, D4S2366, and D5S1719 were assembled by genotyping database samples from known racial groups.

Example 4
DNA Sequencing of Selected Alleles

Isolation of Alleles for Sequence Analysis

Each allele sequenced was amplified (simplex) with non-labeled primers. The amplicons were loaded onto a 4% polyacrylamide sequencing gel and separated by size with electrophoresis. 1×TBE gel and 1×TBE electrophoresis buffer. Following electrophoresis, each gel containing size-separated amplicons was stained with silver nitrate. Alleles were determined by size and bands for each were cut from the polyacrylamide gels using a razor blade. Each gel slice was crushed in ddH2O and then incubated at 4° C. for greater than 24 hours. Gel debris was pelleted by centrifugation at 12,000×g for 2 minutes. Ten microliters of supernatant was then used as a template in a secondary PCR amplification using the original primers sets for each system.

Resultant amplicons were again size separated by polyacrylamide gel electrophoresis to check the validity of each reaction. Positive PCR samples were then cleaned up (dNTP and primer removal) and microconcentrated using the Ultrafree-MC Filters (30K cutoff) from Millipore. Sequencing reactions were performed using the ABI Prism 377 Automatic Sequencer and the Dye Terminator Cycle Sequencing Ready Reaction Kit with Amplitaq Polymerase, FS from ABI. Comonents of the 20.0 ul Cycle Sequenicing Reaction were 8.0 ul of terminator ready reaction mix, 4.0 ul of template double stranded DNA (0.2 ug/ul), 3.2 ul of primers (3.2 pmole) and 4.8 ul of water.

Cycle sequencing reaction conditions were a DNA denaturing step at 96O C for 30 seconds, followed by 25 Cycles of 96O C for 10 seconds, 50O C for 5 seconds, and 60O C for 4 minutes. Following Cycle Sequencing Reaction, the entire 20.0 ul reaction was precipitated in 95% ethanol for 10 minutes on ice. The precipitated DNA was centrifuged for 30 minutes at 12,000×g for 30 minutes. The supernatant was removed by pouring and the pellet was air-dried for 10 minutes. The pellet was resuspended in 6.0 ul of loading buffer (Deionized formamide, 25.0 mMEDTA(pH 8.0), 50 mg/ml Blue Dextran with aratio of 5:1 formamide to EDTA/Blue Dextran). Each sample was vortexed and pulse centrifuged to collect sample at the bottom of the tube. The DNA was denatured at 9°Celsius for 2 minutes and then placed on ice. 1.5 ul of each sample was loaded into every other lane of a 4% polyacrylamide gel connected to the ABI Prism 377.

D18S535 Allele Sequences

A 134 bp (SEQ ID NO: 15) and a 150 bp (SEQ ID NO: 16) allele were isolated from sample F1938 (African American male), and sequenced as described above. FIGS. 2A and 2B show the DNA sequences (5' to 3') of the 134 bp and 150 bp allelic PCR fragments for D18S535 as defined by the primers (lower case). The fragments differed only by the number of GATA repeats (bold) they possessed. The two alleles had variable GATA STR regions with the 150 bp fragment possessing 14 GATA repeats and the 134 bp fragment possessing 10 GATA repeats. The flanking regions in the two alleles were identical. Since no alleles were observed that did not differ from other alleles by multiples of 4 bp, it is likely that the population variability observed for this STR locus was entirely due to differences in number of GATA repeats.

D22S683 Allele Sequences

A 176 bp allele (SEQ ID NO: 17) was isolated from specimen F1572 (African American male) and a 200 bp allele (SEQ ID NO: 18) was isolated from specimen B7 (African American male) as described above. Both alleles were sequenced as described above. FIGS. 3A and 3B show the DNA sequences (5' to 3') of the 176 bp and 200 bp allelic amplified fragments of the D22S683 locus with the primer sequences shown in lower case. The flanking sequences of these two alleles were identical. The difference in size of the two fragments is accounted for by variability in repeat number of two adjacent regions: a GATA repeat region (bold) and a TAGATA repeat region (bold, underlined). This type of variability is termed herein a Class I CTR and provides a far greater amount of polymorphism at the population level, as evidenced by the data collected for the four major racial groups in the United States.

In order to describe these alleles more conveniently, it was decided to name them by their GATA-equivalents. For example, an allele with the composition [GATA]$_9$ [TAGATA]$_2$ would be indistinguishable from a [GATA]$_{12}$ allele and would be called a 12 repeat allele. Using accepted nomenclature, the 176 bp allele would be called a 13.2 repeat allele (13 full GATA repeat equivalents plus 2 bp), and the 200 bp allele would be called a 19.2 allele.

Interestingly, there were some alleles discovered in the population database that differ from the full and half repeat alleles by one base pair. It is not yet clear where this variability arises at the nucleotide level, but it is easily detectable on sequencing gels. Thus, the complex tandem repeat D22S683 shows an extremely high degree of population variability at the nucleotide level, making it a powerful component of the multiplex described herein.

D9S302 Allele Sequences

A 262 bp allele (SEQ ID NO: 19) was isolated from specimen M 1900 (African American female) and a 274 bp allele (SEQ ID NO: 20) was isolated from specimen F1453 (African American male). Because of their larger size only partial sequences of the D9S302 amplicon have been obtained by the cycle sequencing technique described above. FIGS. 4A and 4B show the DNA sequences (5' to 3') of the 262 bp and 274 bp allelic amplified fragments for D9S302 with primers shown in lower case letters. The flanking sequences remain undetermined. GATA sequences are shown in bold. It is apparent from the partial sequences of the 262 bp and 274 bp alleles that there were two to several GATA tandem repeat regions separated by non-GATA sequences. This GATA repeat region is termed herein a Class II CTR and it displayed a high level of population variability, as did the D22S683 complex repeat region described above. When the actual number of GATA repeats are determined, alleles will be described by how many repeats they contain. They were described herein simply by the size of the allelic fragments in base pairs for the purpose of performing population genetic tests on the three loci which comprise the multiplex.

D3S2387 Allele Sequences

The D3S2387 locus is a complex repeat system containing a string of CT dinucleotide repeats followed by a non-repeat island of ATCTCCA and then the four-nucleotide repeats of GACA and GATA. The published GenBank sequence for D3S2387 is a 191 bp PCR fragment which contains 10 CT repeats and 26 GACA/GATA repeats (FIG. 5A, SEQ ID NO: 21). We designated this size PCR fragment Allele 26. Several alleles were sequenced and the actual repeat number/size of the PCR fragment was determined. All sequencing reactions were performed using the ABI PRISM 377 Automated DNA Sequencer and the Ready Reaction for dye-terminator sequencing. The 183 bp allele from H62 (Hispanic sample) has 10 CT repeats and 24 GACA/GATA and is Allele 24 (FIG. 5B, SEQ ID NO: 22). The 185 bp allele from (Hispanic sample) has 15 CT repeats and 22 GACA/GATA repeats and is designated Allele 24.2 (FIG. 5C, SEQ ID NO: 23). The designation of allele 24.2 follows the D22S683 precedent and (CT)$_{15}$(GATA/GACA)$_{22}$ is the equivalent of 24.2 GATA repeats. There are 10 CT repeats and 27 GACA/GATA repeats in the 195 bp allele from #7057=1331-01 (positive CEPH specific control sample) which is designated Allele 27 (FIG. 5D, SEQ ID NO: 24). The 215 bp allele from F1731 (Caucasian male) has 10 CT repeats and 32 GACA/GATA repeats and is designated Allele 32 (FIG. 5E, SEQ ID NO: 25).

D4S2366 Allele Sequences

The D4S2366 locus is a complex system that has GATA repeats in the downstream primer. In FIGS. 6A–6C, primer sequences are shown in lower case, GATA repeats are in bold, and any GATT sequences are bold and underlined. The GenBank sequence for D4S2366 is 131 bp (+1 for A+=132) (FIG. 6A, SEQ ID NO: 26). It has a series of GATA repeats interrupted by islands of non-repeat DNA sequence, 13 GATA repeats and 1 GATT. The 131 bp PCR fragment of D4S2366 has been designated Allele 14. A 123 bp fragment from 1331-01 (positive control sample) was sequenced and has 11 GATA repeats and 1 GATT (FIG. 6B, SEQ ID NO: 27). Therefore, the 123 bp PCR fragment of D4S2366 has been designated Allele 12. A 143 bp allele from F7866 (Japanese male) has 15 GATA repeats and 2 GATT and is designated Allele 17 (FIG. 6C, SEQ ID NO: 28).

D5S1719 Allele Sequences

This locus is a Class II CTR. In FIGS. 7A–7D, primer sequences are shown in lower case, GATA repeats are in bold, and any GAT sequences are in bold and underlined. The GenBank report indicates that the 88 bp fragment has 7 GATA repeats. Therefore, the 88 bp fragment has been designated Allele 7 (FIG. 7A, SEQ ID NO: 29). A 107 bp allele from M1449 (Caucasian female) has 11 GATA repeats and a single GAT and has been designated Allele 11.3 (FIG. 7B, SEQ ID NO: 30). An 84 bp allele from F1410 (Caucasian male) has 6 GATA repeats and is designated Allele 6 (FIG. 7C, SEQ ID NO: 31). An 88 bp allele from M1459 (Caucasian female) matches the published GenBank sequence, having 7 GATA repeats and is designated Allele 7 (FIG. 7D, SEQ ID NO: 32).

D7S1804 Allele Sequences

This is a complex locus with a string of GATA and GACA repeats interrupted by islands of non-repeat DNA sequence. The GenBank sequence is 259 bp and has 24 CTAT repeats, 4 CTGT repeats and is designated Allele 28 (FIG. 8A, SEQ ID NO: 33). In FIGS. 8A–8E, primer sequences are shown in lower case, CTAT repeats are in bold, and CTGT repeats are in bold and underlined. A 237 bp allele from B29 (Black) has 18 CTAT repeats, 4 CTGT repeats and is called Allele 22 (FIG. 8B, SEQ ID NO: 34). A 297 bp allele from M1563 (Caucasian female) has 30 CTAT repeats, 7 CTGT repeats and is designated Allele 37 (FIG. 8C, SEQ ID NO: 35). A 289 bp allele from 1331-01 (positive control) has 28 CTAT repeats, 7 CTGT repeats and is called Allele 35 (FIG. 8D, SEQ ID NO: 36). A 265 bp allele from 1331-01 (positive control) has 25 CTAT repeats, 4 CTGT repeats and is called Allele 29 (FIG. 8E, SEQ ID NO: 37).

Other embodiments and uses of the invention will be apparent to those skilled in the art from consideration of the specification and practice of the invention disclosed herein. Accordingly, it should be understood that the methods described in the foregoing description are illustrative only, and not intended as a limitation on the scope of the invention. All documents, U.S. patents and patent applications, including U.S. patent application Ser. No. 09/055,188, filed Apr. 6, 1998 and U.S. patent application Ser. No. 08/637,155, filed Apr. 24, 1996, disclosed herein are specifically incorporated by reference. The specification and examples should be considered exemplary only within the true scope of the invention indicated by the following claims.

What is claimed is:

1. A method of multiplex amplification of DNA molecules comprising a plurality of loci, the method comprising:
   i) providing at least two loci, and
   ii) amplifying the loci in a single amplification reaction, wherein at least one locus of said plurality of loci is selected from the group consisting of D3S2387, D4S2366, D5S1719, and D7S1804.

2. The method of claim 1, wherein said plurality of loci comprises at least three loci selected from the group consisting of D3S2387, D4S2366, D5S1719 and D7S1804.

3. The method of claim 2, wherein said plurality of loci comprises D3S2387, D4S2366, D5S1719 and D7S1804.

4. The method of claim 1, wherein said plurality of loci further comprises at least one additional locus selected from the group consisting of D9S302, D22S683 and D18S535.

5. The method of claim 4, wherein said plurality of loci comprises D9S302, D22S683 and D18S535.

6. The method of claim 1, wherein said plurality of loci further comprises at least one additional locus selected from the group consisting of CSFIPO, FESFPS, TH01, and LIPOL.

7. The method of claim 6, wherein said plurality of loci comprises CSFIPO, FESFPS, TH01, and LIPOL.

8. The method of claim 1, wherein sad plurality of loci comprises at least one locus selected front the group consisting of D3S2387, D4S2366, D5S1719 and D7S18804, at least one locus selected from the group consisting of D9S302, D22S683 and D18S535, and at least one locus selected from the group consisting of CSFIPO, FESFPS TH01 and LIPOL.

9. The method of claim 8, wherein said plurality of loci comprises D3S2387, D4S2366, D5S1719, D7S1804, D9S302, D22S683, D18S535, CSFIPO, FESFPS, TH01 and LIPOL.

10. The method of claim 1, wherein said amplification reaction comprises reagents, a template DNA, magnesium and at leas two locus-specific primers.

11. The method of claim 10, wherein the locus-specific primers are selected from the group consisting of SEQ.ID. NOS.: 1–14 and combinations thereof.

12. The method of claim 1, wherein the amplification reaction is selected from among polymerase chain reaction (PCR), Qβ replication, isothermal replication and ligase chain reaction.

13. The method of claim 12, wherein the amplification reaction is a polymerase chain reaction comprising triphasic cycles, wherein the total number of triphasic cycles ranges from 10–40 cycles and wherein each cycle comprises:
   i) a first step having a duration of 20 seconds to 5 minutes carried out at a temperature of 90° C. to 98° C.;
   ii) a second step having a duration of 20 seconds to 5 minutes carried out at a temperature of 40° C. to 65° C.; and iii) a third step having a duration of 20 seconds to 10 minutes carried out at a temperature of 60° C. to 77° C.

14. The method of claim 13, wherein,
   i) the first step has a duration of 45 seconds and is carried out at 95° C.;
   ii) the second step has a duration of 45 seconds and is carried out at 59° C.; and
   iii) the third step has a duration of 45 seconds and is carried out at 72° C.

15. The method of claim 13, comprising 25–30 triphasic cycles.

16. The method of claim 13, wherein the polymerase chain reaction further comprises a heating step prior to the initial triphasic cycle.

17. The method of claim 16, wherein the heating step has a duration of 20 seconds to 10 minutes and is carried out at a temperature of 94° C. to 95° C.

18. The method of claim 13, wherein the polymerase chain reaction further comprises a holding phase after each cycle.

19. The method of claim 18, wherein the holding phase has a duration of 5–10 minutes and is carried out at a temperature of 68° C. to 74° C.

20. The method of claim 13, further comprising a cooling phase after the third step of the final cycle, wherein the cooling phase has a duration greater than 5 minutes and is carried out at a temperature of 4° C. to 15° C.

21. The method of claim 18, further comprising a cooling phase after a final holding phase, wherein the cooling phase has a duration greater than 5 minutes and is carried out at a temperature of 4° C. to 15° C.

22. The method of claim 13, wherein the polymerase chain reaction comprises:
   i) an initial heating step having a duration of 10 minutes carried out at 95° C., prior to the first cycle;
   ii) 28 triphasic cycles, each comprising:
      a) a first step having a duration of 45 seconds carried out at 95° C.;
      b) a second step having a duration of 45 seconds carried out at 59° C.; and
      c) a third step having a duration of 45 seconds carried out at 72° C.;
   iii) a holding phase after each triphasic cycle having a duration of 7 minutes carried out at 72° C.; and
   iv) a final cooling phase having a duration of greater than 5 minutes carried at 4° C.

23. The method of claim 13, wherein the polymerase chain reaction comprises:
   i) an initial heating step having a duration of 10 minutes carried out at 94.5° C., prior to the first cycle;
   ii) 27 triphasic cycles, each comprising:
      a) a first step having duration of 45 seconds carried out at 95° C.;
      b) a second step having a duration of 45 seconds carried out at 59° C. and the duration of the step is 45 seconds; and
      c) a third step having a duration of 45 seconds carried out at 72° C.;
   iii) a holding phase after each triphasic cycle having a duration of 7 minutes carried out at 72° C.; and
   iv) a final cooling phase having a duration greater than 5 minutes carried out at 4° C.

24. A kit for multiplex amplification of DNA molecules comprising a plurality of loci wherein the kit comprises:
   i) reagents for a DNA amplification reaction, and
   ii) reagents for isolation and/or identification of DNA molecules comprising at least one locus selected from the group consisting of D3S2387, D4S2366, D5S1719, and D7S1804.

25. The kit of claim 24, wherein the DNA molecules further comprise at least one locus selected from the group consisting of D9S302, D22S683, D18S535.

26. The kit of claim 24, wherein the DNA molecules further comprise at least one locus selected from the group consisting of CSFIPO, FESFPS, TH01, and LIPOL.

27. The kit of claim 24, wherein the DNA molecules comprise the D3S2387, D4S2366, D5S1719, D7S1804, D9S302, D22S683, D18S535, TH01, and LIPOL loci.

28. The kit of claim 24, wherein the amplification reaction is a polymerase chain reaction (PCR) and the reagents for isolation and/or identification of the DNA molecules comprise locus-specific primers.

29. The kit of claim 28, wherein the primers are selected from the group consisting of SEQ.ID.NOS.: 1–14 and combinations thereof.

* * * * *